US010851059B2

(12) United States Patent
Kleinbeck-Riniker et al.

(10) Patent No.: US 10,851,059 B2
(45) Date of Patent: Dec. 1, 2020

(54) PROCESSES AND INTERMEDIATES FOR NEP INHIBITOR SYNTHESIS

(71) Applicant: Novartis AG, Basel (CH)

(72) Inventors: Florian Karl Kleinbeck-Riniker, Zurich (CH); Ives Mafli, Zurich (CH); Benjamin Martin, Leymen (FR); Gerhard Penn, Oberwil (CH); Gottfried Sedelmeier, Schallstadt (DE); Joerg Sedelmeier, Weil am Rhein (DE); Francesco Venturoni, Saint-Louis (FR)

(73) Assignee: Novartis AG, Basel (CH)

( * ) Notice: Subject to any disclaimer, the term of this patent is extended or adjusted under 35 U.S.C. 154(b) by 56 days.

(21) Appl. No.: 16/325,880

(22) PCT Filed: Aug. 16, 2017

(86) PCT No.: PCT/IB2017/054976
§ 371 (c)(1),
(2) Date: Feb. 15, 2019

(87) PCT Pub. No.: WO2018/033866
PCT Pub. Date: Feb. 22, 2018

(65) Prior Publication Data
US 2019/0202785 A1      Jul. 4, 2019

(30) Foreign Application Priority Data

Aug. 17, 2016   (EP) .................................... 16184589

(51) Int. Cl.
| | | |
|---|---|---|
| *C07C 271/22* | (2006.01) | |
| *C07D 213/16* | (2006.01) | |
| *C07C 201/12* | (2006.01) | |
| *C07C 251/38* | (2006.01) | |
| *C07C 201/16* | (2006.01) | |
| *C07C 205/53* | (2006.01) | |
| *C07C 249/08* | (2006.01) | |
| *C07D 213/36* | (2006.01) | |
| *C07C 205/51* | (2006.01) | |
| *C07C 67/347* | (2006.01) | |
| *C07C 231/02* | (2006.01) | |
| *C07C 269/00* | (2006.01) | |
| *C07C 201/06* | (2006.01) | |
| *C07C 227/18* | (2006.01) | |
| *C07C 45/49* | (2006.01) | |
| *C07C 229/06* | (2006.01) | |
| *C07C 249/02* | (2006.01) | |
| *C07D 207/267* | (2006.01) | |
| *C07D 207/12* | (2006.01) | |

(52) U.S. Cl.
CPC ............ *C07D 213/16* (2013.01); *C07C 45/49* (2013.01); *C07C 67/347* (2013.01); *C07C 201/06* (2013.01); *C07C 201/12* (2013.01); *C07C 201/16* (2013.01); *C07C 205/51* (2013.01); *C07C 205/53* (2013.01); *C07C 227/18* (2013.01); *C07C 229/06* (2013.01); *C07C 231/02* (2013.01); *C07C 249/02* (2013.01); *C07C 249/08* (2013.01); *C07C 251/38* (2013.01); *C07C 269/00* (2013.01); *C07C 271/22* (2013.01); *C07D 207/267* (2013.01); *C07D 213/36* (2013.01); *C07B 2200/07* (2013.01); *C07D 207/12* (2013.01)

(58) Field of Classification Search
CPC .................................................. C07C 271/22
See application file for complete search history.

(56) References Cited

U.S. PATENT DOCUMENTS 10,385,004 B2 * 8/2019 Martin .................. C07C 201/12

FOREIGN PATENT DOCUMENTS

WO   2008/083967 A2   7/2008

OTHER PUBLICATIONS

Agami et al., "Influence of the Ester Group During the Enantioselective Methylation of [alpha]-aldehyde esters viatheir chiral oxazolidine derivatives", Tetrahedron Letters, 28(46):5659-5660. 1987.
Kessar et al., "Synthetic studies 3 in steroidal sapogenins and alkalods-X", Tetrahedron, 27(13):2869-2875. 1971.
Kollar et al., "Asymmetric hydroformylation of unsaturated esters with PtCl (SnCl3) [(R.R)-DIOP] catalyst", Journal of Organometallic Chemistry, 330(102):305-314. 1987.
Chougnet et al, "Diastereoselective and Highly Enantioselective Henry Reactions using C1-Symmetrical Copper(II) Complexes", Advanced Synthesis & Catalysis, 353(10):1797-1806. 2011.
Corse et al., "Dihydrozeatin: An Improved Synthesis and Resolution of Both Isomers", Journal of Plant Growth Regulation, 2:47-57, (1983).

* cited by examiner

*Primary Examiner* — John S Kenyon
(74) *Attorney, Agent, or Firm* — Judith D. Kuntz

(57) ABSTRACT

The present invention relates to a new chemical synthesis, intermediates and catalysts useful for the preparation of the neprilysin (NEP) inhibitor sacubitril, inter alia via nitro 5 compounds. It further relates to new intermediate compounds and their use for said new chemical synthesis route, as well as a new catalyst ligand.

14 Claims, No Drawings

PROCESSES AND INTERMEDIATES FOR NEP INHIBITOR SYNTHESIS

RELATED APPLICATIONS

This application is a national stage application, filed under 35 U.S.C. § 371, of International Application No. PCT/IB2017/054976, filed Aug. 16, 2017, which claims priority to and the benefit of, European Patent Application No. 16184589.6, filed Aug. 17, 2016, the entire contents of which are incorporated herein by reference in their entireties.

FIELD OF THE INVENTION

The present invention relates to a new chemical synthesis route and intermediates useful for the preparation of neprilysin (NEP) inhibitors and their prodrugs, in particular for the NEP inhibitor prodrug sacubitril.

BACKGROUND OF THE INVENTION

The NEP inhibitor prodrug sacubitril (N-(3-carboxyl-1-oxopropyl)-(4S)-(p-phenylphenylmethyl)-4-amino-(2R)-methyl butanoic acid ethyl ester; IUPAC name 4-{[(1S,3R)-1-([1,1'-Biphenyl]-4-ylmethyl)-4-ethoxy-3-methyl-4-oxobutyl]amino}-4-oxobutanoic acid) is represented by the following formula (A)

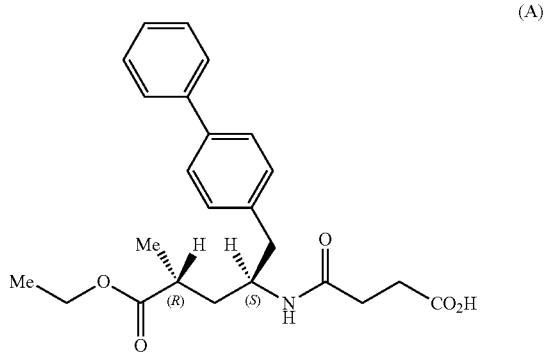

Sacubitril together with valsartan, a known angiotensin receptor blocker (ARB), forms a sodium salt hydrate complex, known as LCZ696, comprising the anionic forms of sacubitril and valsartan, sodium cations and water molecules in the molar ratio of 1:1:3:2.5, respectively (ratio of 6:6:18:15 in the asymmetric unit cell of the solid state crystal), which is schematically present in formula (B).

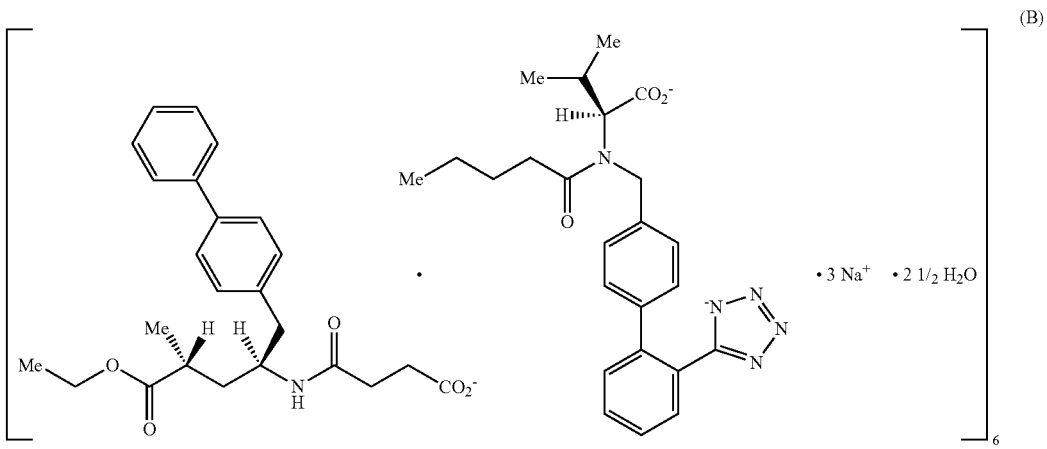

Said complex is also referred to by the following chemical names: Trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate or Octadecasodium hexakis(4-{[(1S,3R)-1-([1,1'-biphenyl]-4-ylmethyl)-4-ethoxy-3-methyl-4-oxobutyl]amino}-4-oxobutanoate) hexakis(N-pentanoyl-N-{[2'-(1H-tetrazol-1-id-5-yl)[1,1'-biphenyl]-4-yl]methyl}-L-valinate)-water (1/15) (IUPAC nomenclature).

LCZ696 acts as angiotensin receptor neprilysin inhibitor (ARNI) and is therefore useful particularly in the treatment of hypertension or chronic heart failure. Its utility has been confirmed by clinical trials, e.g. in the landmark PARADIGM-HF trial. Meanwhile, on Jul. 7, 2015, the FDA has approved LCZ696 for marketing.

Chemical synthesis routes to prepare NEP inhibitors and their prodrugs, in particular sacubitril, and its precursors have been described previously, e.g. in Ksander et al. *J. Med. Chem.* 1995, pp. 1689-1700; in U.S. Pat. No. 5,217,996 and in the international patent applications WO 2007/083774, WO 2007/083776, WO 2008/031567, WO 2008/083967, WO 2008/120567, WO 2009/090251, WO 2010/081410, WO 2011/035569, WO 2011/088797, WO 2012/025501, WO 2012/025502, WO 2013/026773, WO 2014/032627, and WO 2015/024991, as well as in CN patent applications CN102260177, CN103483201, CN104557600, CN104725256, CN104725279, CN105017082, CN105061263, CN105085322, CN105152980, CN105168205, CN105198775, CN105237560, CN105330569, CN105481622, CN105566194 and CN105601524 and others.

However, there is still a need to design a chemical process for the synthesis of sacubitril ("the drug substance") which is suitable for industrial scale production under economically and environmentally favourable conditions and allows to provide the drug substance in high chemical purity and with high stereochemical selectivity.

SUMMARY OF THE INVENTION

The invention relates to novel intermediates and process steps and processes for the manufacture of a compound (1) represented below, and its further use in the manufacture of sacubitril. It also relates to novel catalysts.

In a first aspect, the present invention provides the following new compounds:

Embodiment 1

A compound of formula (1) or a salt thereof,

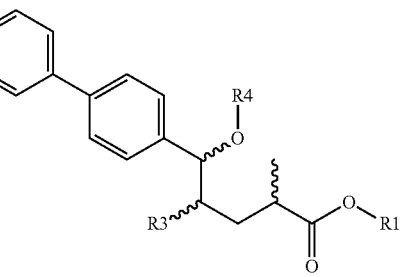
(1)

wherein R1 is hydrogen or $C_1$-$C_6$-alkyl, preferably ethyl, and R3 is —$NO_2$ or —NR'R", wherein R' and R" are independently of each other hydrogen or a nitrogen protecting group, preferably R3 is —$NO_2$ or —NHR' wherein R' is a nitrogen protecting group, preferably tert-butyloxycarbonyl, and R4 is selected from hydrogen, $C_1$-$C_6$-carbonyl, $C_1$-$C_6$-alkoxycarbonyl and a sulphonyl group, preferably hydrogen.

In one embodiment thereof, the compound of the formula (1) is represented by formula (1-R) with the following stereochemistry

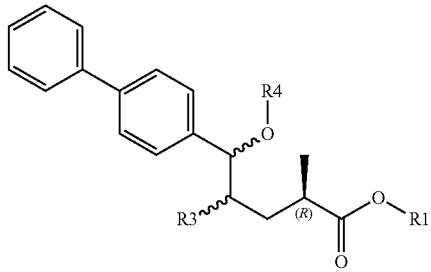
(1-R)

wherein R1, R3 and R4 are as defined for the compound of formula (1).

In another embodiment thereof, the compound of the formula (1) is represented by formula (1-RS) with the following stereochemistry

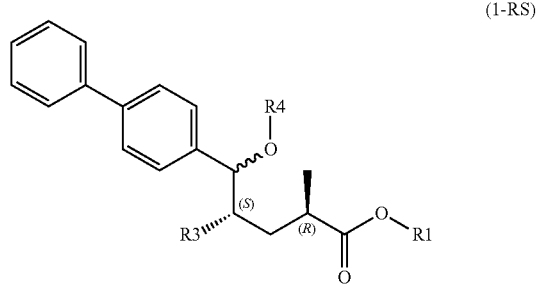
(1-RS)

wherein R1, R3 and R4 are as defined for the compound of formula (1).

Embodiment 2

A compound of formula (2) or a salt thereof,

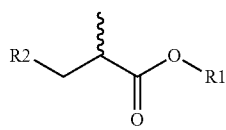
(2)

wherein R1 is hydrogen or ethyl, and R2 is [(E)- or (Z)-formoximyl] —CHNOH, or [nitro-methylene]-$CH_2NO_2$, preferably R2 is —$CH_2NO_2$.

In one embodiment thereof, the compound of formula (2) is represented by formula (2-R) with the following stereochemistry

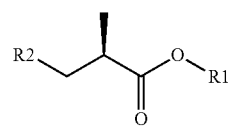
(2-R)

wherein R1 and R2 are as defined for the compound of formula (2).

In one embodiment thereof, the compound of formula (2-R) wherein R1 is ethyl and R2 is —$CH_2NO_2$, is represented by formula (2-a-R-Et)

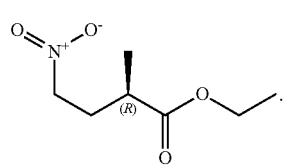
(2-a-R-Et)

Embodiment 3

A compound of formula (4b)

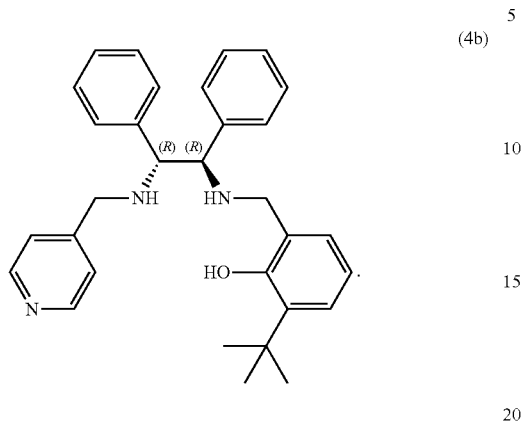

In a second aspect, the present invention provides a new process for the manufacture of the compound of the formula (6) or a salt thereof, as defined herein. This process comprises several steps via novel intermediate compounds and is depicted in the following Schemes 1 to 4, respectively, wherein the individual processes depicted in each SCHEME 1-4 represent separate embodiments of the invention.

SCHEME 1

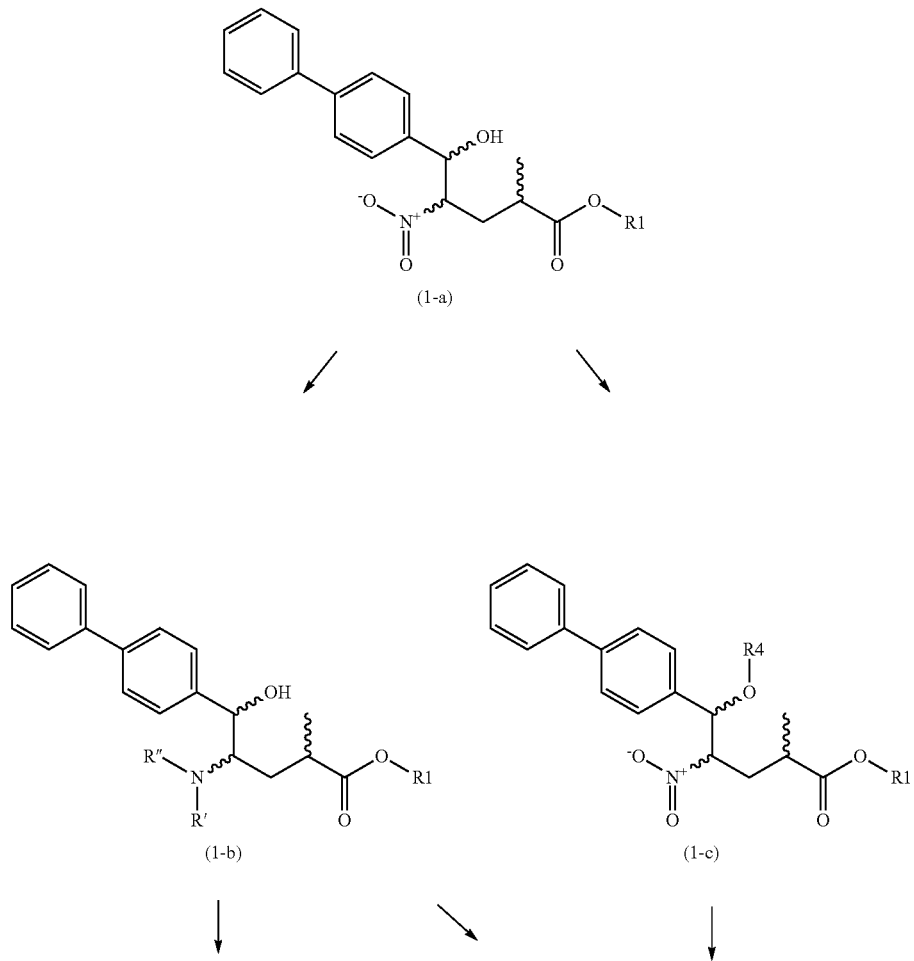

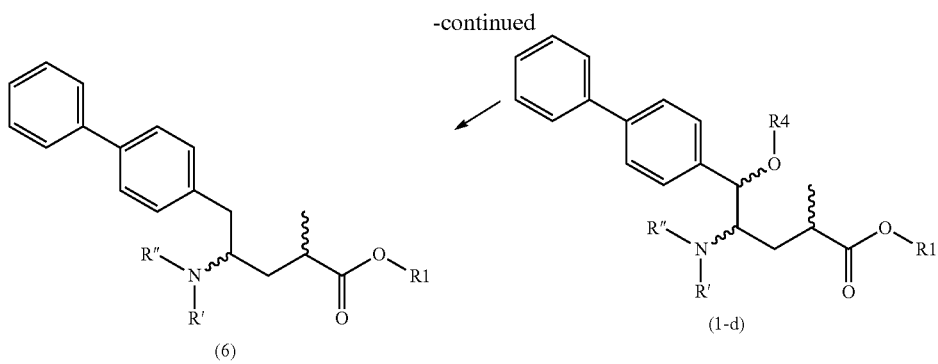

SCHEME 1 depicts the process comprising transformation of the novel intermediate compound of formula (1-a), wherein R1 is hydrogen or $C_1$-$C_6$-alkyl, preferably ethyl, into a compound of formula (6), wherein R' and R" are independently of each other hydrogen or a nitrogen protecting group, preferably tert-butyloxycarbonyl, and R1 is hydrogen or $C_1$-$C_6$-alkyl, especially ethyl, via hydrogenation, optionally comprising the introduction of an OH-activating group R4, preferably selected from $C_1$-$C_6$-carbonyl, $C_1$-$C_6$-alkoxycarbonyl and a sulfonyl group, and/or a nitrogen protecting group R' and/or R".

If desired—and not explicitly disclosed in the SCHEME 1—this can be followed by converting a compound of the formula (6), wherein each of R' and R" are hydrogen, into a salt, e.g. with an acid. Alternatively, the reduction can take place with parallel introduction of a nitrogen protecting group or the nitrogen protecting group can be added subsequently.

The novel compound of formula (1-a) can be obtained according to the process as depicted in the following SCHEME 2, which represents a key embodiment of the present invention:

SCHEME 2

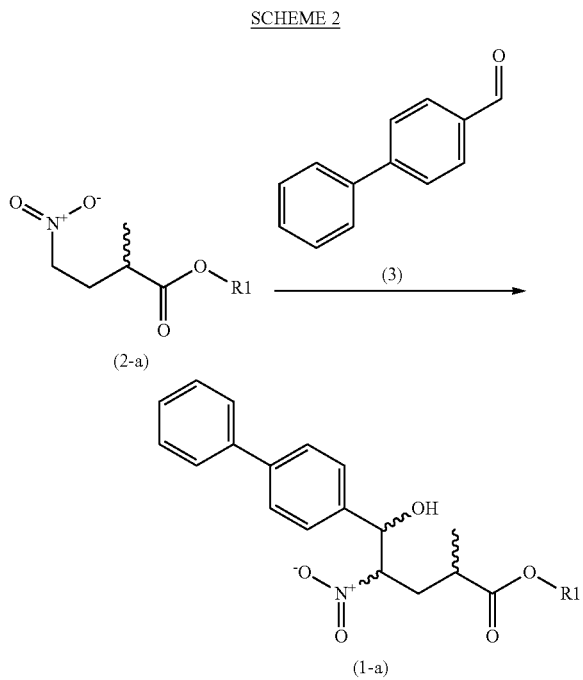

SCHEME 2 depicts a process for the manufacture of a compound of the formula (1-a), said process comprising reacting a compound of formula (2-a) with a compound of formula (3) in the presence of a catalyst, preferably a metal complex catalyst, for a Henry reaction, wherein R1 is hydrogen or $C_1$-$C_6$-alkyl, preferably ethyl.

The compound of formula (2-a) can be obtained according to the following SCHEMES 3A or 3B:

SCHEME 3A:

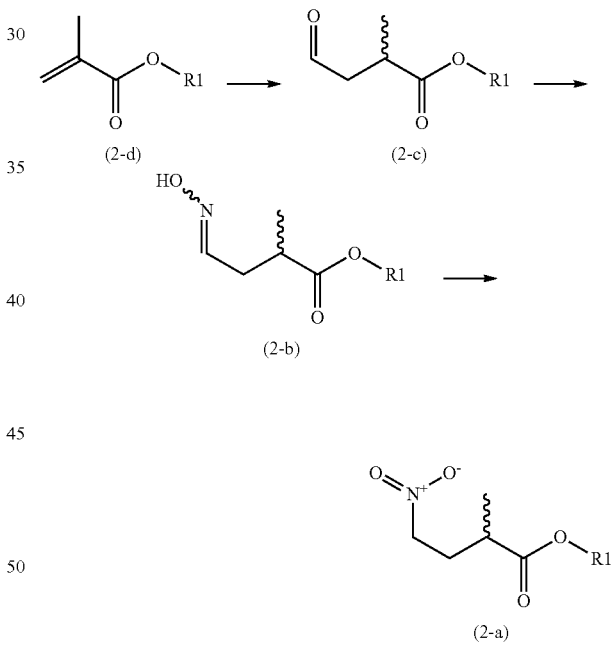

SCHEME 3A depicts a process for the manufacture of a compound of the formula (2-a), said process comprising submitting a methacrylate compound of formula (2-d) to a hydroformylation reaction to obtain a compound of formula (2-c), converting the compound of formula (2-c) into the corresponding oxime of formula (2-b) and then oxidizing the oxime of formula (2-b) to obtain the nitro derivative of formula (2-a), wherein for all compounds R1 is hydrogen or $C_1$-$C_5$-alkyl, preferably ethyl. In one embodiment, the hydroformylation is carried out in the presence of a catalyst to obtain the desired enantiomer of the compound of formula (2-c).

SCHEME 3B:

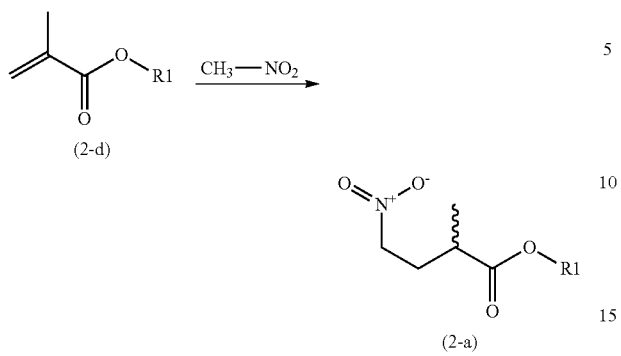

SCHEME 3B depicts a process for the manufacture of a compound of the formula (2-a), said process comprising reacting a methacrylate compound of formula (2-d) with nitromethane wherein for all compounds R1 is hydrogen or $C_1$-$C_6$-alkyl, preferably ethyl.

The compound of formula (2-a-R) can be obtained by a chiral separation of the compound of formula (2-a) as depicted in SCHEME 4:

SCHEME 4:

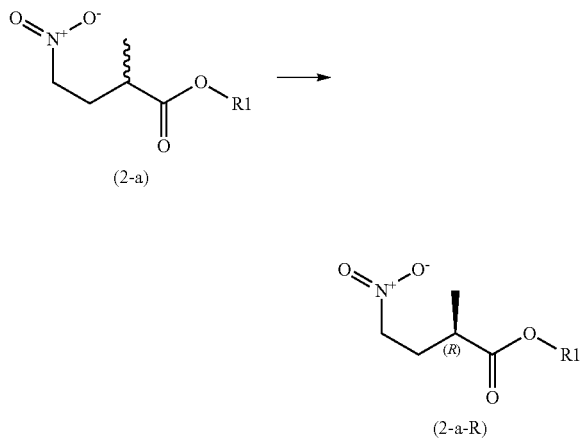

Finally, a compound according to formula (6) or salt thereof can be further reacted to obtain the NEP inhibitor or NEP inhibitor pro-drug of formula (8) according to the following SCHEME 5:

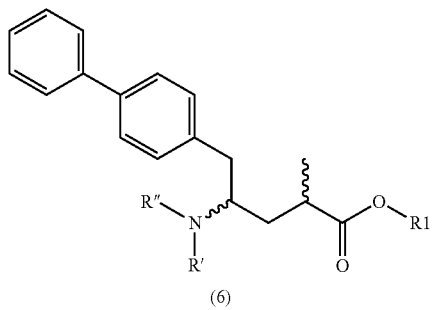

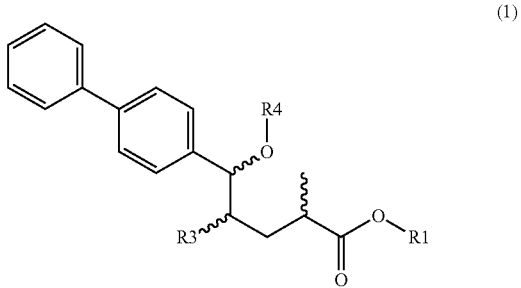

wherein for all compounds R1 is hydrogen or $C_1$-$C_6$-alkyl, preferably ethyl, and R' and R'' are independently of each other hydrogen or a nitrogen protecting group, preferably tert-butyloxycarbonyl.

In a third aspect, the present invention provides a new use of the novel compound of formula (1)

(1)

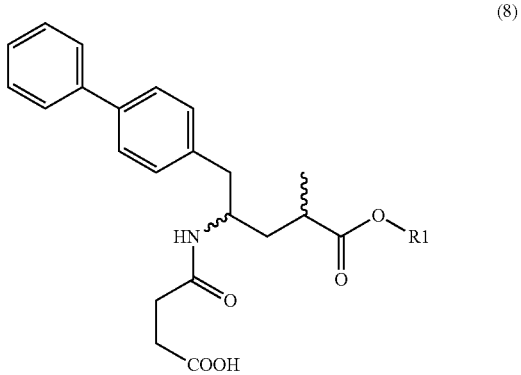

wherein R1 is hydrogen or $C_1$-$C_6$-alkyl, preferably ethyl, R3 is —NR'R'', or —NO$_2$ and R' and R'' are independently of each other hydrogen or a nitrogen protecting group, preferably R3 is —NHR' and R' is tert-butyloxycarbonyl, and R4 is selected from hydrogen, $C_1$-$C_6$-carbonyl, $C_1$-$C_6$-alkoxycarbonyl and a sulphonyl group, preferably hydrogen, in the preparation of a compound of formula (8)

(8)

wherein R1 is hydrogen or $C_1$-$C_6$-alkyl, preferably ethyl, preferably in the preparation of N-(3-carboxyl-1-oxopropyl)-(4S)-(p-phenylphenylmethyl)-4-amino-(2R)-methyl butanoic acid, or salts thereof, or N-(3-carboxyl-1-oxopropyl)-(4S)-(p-phenylphenylmethyl)-4-amino-(2R)-methyl butanoic acid ethyl ester or salts thereof.

In further aspects and embodiments, the invention relates to any one or more of the novel compounds, processes and catalysts represented in the claims which are incorporated here by reference.

The invention also relates to any sequential combination of the process steps described above and below.

In its above mentioned aspects which are also given in more detail below the present invention provides the following advantages: The synthesis route is suitable for industrial scale processing. The synthesis route is economically and environmentally favorable. The compound of formula (1), in particular of formula (1-b-RS), which is desired for the synthesis of sacubitril is produced in high yield and high stereoselectivity by the asymmetric Henry reaction involved in this synthesis route which requires only a moderate to low loading of the catalyst and prevents to a large extent undesired retro-Henry reactions, side-reactions such as the elimination of water, Canizzaro or aldol-condensation reactions and especially double Henry reaction amazingly is not observed, that is, no reaction of one nitroester with two aldehyde molecules).

DETAILED DESCRIPTION OF THE INVENTION

General Terms

The general definitions used above and below, unless defined differently, have the following meanings, where replacement of one or more or all expressions or symbols by the more specific definitions can be made independently for each invention embodiment and lead to more preferred embodiments.

Where the plural form is used for compounds, starting materials, intermediates, salts, pharmaceutical preparations, diseases, disorders and the like, this intends to mean one (preferred) or more single compound(s), salt(s), pharmaceutical preparation(s), disease(s), disorder(s) or the like, where the singular or the indefinite article ("a", "an") is used, this does not intend to exclude the plural, but only preferably means "one".

Chiral Compounds

The term "chiral" refers to molecules which have the property of non-superimposability on their mirror image partner, while the term "achiral" refers to molecules which are superimposable on their mirror image partner.

In the formulae of the present application the term " ⁀⁀⁀ " on a C-sp$^3$ represents a covalent bond, wherein the stereochemistry of the bond is not defined. This means that the term " ⁀⁀⁀ " on a C-sp$^3$ comprises an (S) configuration as well as an (R) configuration of the respective chiral centre. Furthermore, mixtures, e.g. mixtures of enantiomers such as racemates, are also encompassed by the present invention. Especially preferred are single stereoisomers of the compounds of the formula (1) or (2), especially the specific ones of formula (1-a) and (1-b).

In the formulae of the present application the term " ⁀⁀⁀ " on a C-sp$^2$ represents a covalent bond, wherein the stereochemistry or the geometry of the bond is not defined. This means that the term " ⁀⁀⁀ " on a C-sp$^2$ comprises a (Z) configuration as well as a (E) configuration of the respective double bond. Furthermore, mixtures, e.g., mixtures of double bond isomers are also encompassed by the present invention.

In the formulae of the present application the term " ⁄ " on a C-sp$^3$ indicates the absolute stereochemistry, either (R) or (S).

In the formulae of the present application the term " ⁄ " on a C-sp$^3$ indicates the absolute stereochemistry, either (R) or (S).

In the formulae of the present application, the term " ═══ " indicates a C-sp$^3$-C-sp$^3$ bond or a C-sp$^2$-C-sp$^2$ bond.

The compounds of the present, invention can possess one or more asymmetric centers. The preferred absolute configurations are as indicated herein specifically. However, any possible pure enantiomer, pure diastereoisomer, or mixtures thereof, e.g., mixtures of enantiomers, such as racemates, are encompassed by the present invention.

Compounds with a stereogenic center but without indication of a specific configuration are considered mixtures of compounds with the respective configurations, e.g. R,R; R,S; S,R and SS, or pure enantiomers/diastereomers.

Stereoisomeric, especially enantiomeric, purity, is where mentioned referring to all diastereomers of the compound taken together (100%). It is determined by chiral chromatography (examples include HPLC, uPLC and GC) or NMR (with addition of chiral entities and or metals). Specific examples of methods include: chiral HPLC equipped with chiral column Chiralpak ID 4.6 mm ⌀×250 mm, 5 μm (Daicel Corporation, Osaka, Japan) at 25° C.; mobile phase Hept:EtOAc:CH$_3$CN, 90:8:2.

The term "substantially optically pure" compound, as defined herein, refers to a compound obtained by a process according to the invention wherein the compound has an optical purity of at least 70% (ee=enantiomeric excess), more preferably of at least 90% (ee) and most preferably at least 95% (ee) or more, such as 100% (ee).

Prodruqs

The term "pro-drug", as used herein, represents in particular compounds which are transformed in vivo to the parent compound, for example, by hydrolysis in blood, for example as described in T. Higuchi and V. Stella, "Pro-drugs as Novel Delivery Systems", volume 14 of the ACS Symposium Series; Edward B. Roche, editor, "Bioreversible Carriers in Drug Design", American Pharmaceutical Association and Pergamon Press, 1987; H Bundgaard, editor, "Design of Prodrugs", Elsevier, 1985; Judkins et al. *Synthetic Communications* 1996, 26, 4351-4367, and "The Organic Chemistry of Drug Design and Drug Action", second edition, R. B. Silverman (particularly chapter 8, pages 497-557), Elsevier Academic Press, 2004.

Pro-drugs therefore include drugs having a functional group which has been transformed into a reversible derivative thereof. Typically, such prodrugs are transformed to the active drug by hydrolysis. As examples may be mentioned the following:

| Functional Group | Reversible derivative |
|---|---|
| Carboxylic acid | Esters, including e.g. alkyl esters |
| Alcohol | Esters, including e.g. sulfates and phosphates as well as carboxylic acid esters |
| Amine | Amides, carbamates, imines, enamines, |
| Carbonyl (aldehyde, ketone) | Imines, oximes, acetals/ketals, enol esters, oxazolidines and thiazoxolidines |

Pro-drugs also include compounds convertible to the active drug by an oxidative or reductive reaction. As examples may be mentioned:

Oxidative Activation
N- and O-dealkylation
Oxidative deamination
N-oxidation
Epoxidation
Reductive Activation
Azo reduction
Sulfoxide reduction
Disulfide reduction
Bioreductive alkylation
Nitro reduction
NEP Inhibitor The term "NEP inhibitor" describes a compound which inhibits the activity of the enzyme neutral endopeptidase (NEP, EC 3.4.24.11).

In the present invention the terms "NEP-inhibitor" or "NEP-inhibitor prodrug" relates to the substances as such or to salts thereof, preferably pharmaceutically acceptable salts thereof. Examples are sodium, potassium, magnesium, calcium or ammonium salts. Calcium salts are preferred.

The NEP inhibitor prodrug N-(3-carboxy-1-oxopropyl)-(4S)-p-phenylphenylmethyl)-4-amino-(2R)-methylbutanoic acid ethyl ester optionally may be further reacted to obtain the active NEP inhibitor N-(3-carboxy-1-oxopropyl)-(4S)-p-phenylphenylmethyl)-4-amino-(2R)-methylbutanoic acid, either in vitro or in vivo.

Substituent Definitions

Alkyl is defined as a radical or part of a radical as a straight or branch (one or, if desired and possible, more times) carbon chain, such as methyl, ethyl, n- or isopropyl, n-butyl, sec.-butyl or tert.-butyl, pentyl, hexyl or heptyl, and is especially $C_1$-$C_7$-alkyl, preferably $C_1$-$C_8$-alkyl, more preferably $C_1$-$C_4$-alkyl. The terms "$C_1$-$C_7$-", "$C_1$-$C_6$-" and "$C_1$-$C_4$-", respectively, define a moiety with up to and including maximally 7, especially up to and including maximally 6 and 4 respectively, carbon atoms, said moiety being branched (one or more times) or straight-chained and bound via a terminal or a non-terminal carbon.

Cycloalkyl is, for example, $C_3$-$C_7$-cycloalkyl and is, for example, cyclopropyl, cyclobutyl, cyclopentyl, cyclohexyl and cycloheptyl. Cyclopentyl and cyclohexyl are preferred.

Alkoxy is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$-alkoxy is preferred.

Alkanoyl is, for example, $C_2$-$C_8$-alkanoyl and is, for example, acetyl [—C(═O)Me], propionyl, butyryl, isobutyryl or pivaloyl. $C_2$-$C_5$-Alkanoyl is preferred, especially acetyl.

Halo or halogen is preferably fluoro, chloro, bromo or iodo, most preferably, chloro, bromo, or iodo.

Halo-alkyl is, for example, halo-$C_1$-$C_7$-alkyl and is in particular halo-$C_1$-$C_4$-alkyl, such as trifluoromethyl, 1,1,2-trifluoro-2-chloroethyl or chloromethyl. Preferred halo-$C_1$-$C_7$-alkyl is trifluoromethyl.

Alkenyl may be linear or branched alkyl containing a double bond and comprising preferably 2 to 12 carbon atoms, 2 to 10 carbon atoms being especially preferred. Particularly preferred is a linear $C_2$-$C_7$-alkenyl, more preferably $C_2$-$C_4$-alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylene is a bivalent radical derived from $C_{1-7}$-alkyl and is especially $C_2$-$C_7$-alkylene or $C_2$-$C_7$-alkylene and, optionally, can be interrupted by one or more, e.g. up to three oxygen, NR14 or sulfur, wherein R14 is alkyl, each of which can be unsubstituted or substituted, by one or more substituents independently selected from for example, $C_1$-$C_7$-alkyl, $C_1$-$C_7$-alkoxy-$C_1$-$C_7$-alkyl or $C_1$-$C_7$-alkoxy.

Alkenylene is a bivalent radical derived from $C_{2-7}$-alkenyl and can be interrupted by one or more, e.g. up to three oxygen, NR14 or sulfur, wherein R14 is alkyl, and is unsubstituted or substituted by one or more, e.g. up to three substitutents, preferably independently selected from the substituents mentioned above for alkylene.

Aryl being a radical or part of a radical is, for example $C_6$-$C_{10}$-aryl, and is preferably a mono- or polycyclic, especially monocyclic, bicyclic or tricyclic aryl moiety with 6 to 10 carbon atoms, such as phenyl, naphthyl or 9-fluorenyl preferably phenyl, and which can be unsubstituted or substituted, by one or more substituents independently selected from alkyl, alkoxy, alkoxycarbonyl, halo, and phenyl, all as defined above, and in particular selected from $C_1$-$C_7$-alkyl, $C_1$-$C_7$-alkoxy-$C_1$-$C_7$-alkyl or $C_1$-$C_7$-alkoxy.

The term arylalkyl refers to aryl-$C_1$-$C_7$-alkyl, wherein aryl is as defined herein and is for example benzyl.

The term carboxyl refers to —$CO_2H$.

Aryloxy refers to an aryl-O— wherein aryl is as defined above.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 14 (more preferably 5 to 14) ring atoms and with one or more, preferably one to four, heteroatoms, independently selected from nitrogen, oxygen, sulfur, S(═O)— or S—(═O)$_2$, and is unsubstituted or substituted by one or more, e.g. up to three substitutents, preferably independently selected from the group consisting of halo, $C_1$-$C_7$-alkyl, $C_1$-$C_7$-alkoxy, halo-$C_1$-$C_7$-alkoxy, such as trifluoromethoxy and $C_1$-$C_7$-alkoxy-$C_1$-$C_7$-alkoxy. When the heterocyclyl is an aromatic ring system, it is also referred to as heteroaryl. Heterocyclyl is preferably imizazolyl, pyrazolyl, oxazolyl, isoxazolyl, thiazolyl, isothiazolyl, pyridinyl, pyranyl, diazionyl, oxazinyl, thiazinyl, dioxinyl, dithiinyl, azepanyl, oxepanyl, thiepanyl, indolyl, isoindoly, quinolinyl, isoquinolinyl, benzazepinyl, carbazolyl, imidazolidinyl, pyrazolidinyl, oxazolidinyl, isoxazolinidyl, thiazolidy, dioxolanyl, dithiolanyl, furazanyl, oxadiazolyl, thiadiazolyl, dithiazolyl, tetrazolyl, piperidinyl, piperazinyl, morpholinyl, thiomorpholinyl, oxothiomorpholinyl, dioxothiomorpholinyl, dioxanyl, dithianyl, azepanyl, oxepanyl, thiepanyl, or benzo-fused variants thereof.

In heterocyclylalkyl, the heterocyclyl is preferably as just defined and is attached to an alkyl as defined for alkyl. Examples are imidazolylmethyl, pyridylmethyl or piperidinylmethyl.

Acetyl is —C(═O)$C_1$-$C_7$-alkyl, preferably —C(═O)Me.

Sulfonyl (sulphonyl) refers to —S(═O)$_2$—R''' wherein R''' is alkyl, aryl or arylalkyl as defined herein, which is optionally substituted as defined herein, e.g. it is (unsubstituted or substituted) $C_1$-$C_7$-alkylsulfonyl, such as methylsulfonyl, (unsubstituted or substituted) phenyl- or naphthyl-$C_1$-$C_7$-alkylsulfonyl, such as phenylmethanesulfonyl, or (unsubstituted or substituted) phenyl- or naphthyl-sulfonyl; wherein if more than one substituent is present, e.g. one to three substitutents, the substituents are selected independently from cyano, halo, amino, nitro, halo-halo-$C_1$-$C_7$-alkyloxy- and $C_1$-$C_7$-alkyloxy. Especially preferred is $C_1$-$C_7$-alkylsulfonyl, such as methylsulfonyl (mesyl), and (phenyl- or naphthyl)-$C_1$-$C_7$-alkylsulfonyl, such as phenylmethanesulfonyl, as well as substituted groups such as tosyl, brosyl, nosyl, triflyl, or dansyl.

Sulfenyl is (unsubstituted or substituted) $C_{6-10}$-aryl-$C_1$-$C_7$-alkylsulfenyl or (unsubstituted or substituted) $C_{6-10}$-arylsulfenyl, wherein if more than one substituent is present, e.g. one to four substitutents, the substituents are selected independently from nitro, halo, halo-$C_1$-$C_7$-alkyl and $C_1$-$C_7$-alkyloxy.

Imide refers to a (unsubstituted or substituted) functional group consisting of two acyl groups bound to nitrogen, preferably a cyclic group derived from dicarboxylic acids. Especially preferred is succinimidyl derived from succinic acid or phthalimidyl derived from phthalic acid. The imidyl group may be substituted by one or more substituents independently selected from for example, $C_1$-$C_7$-alkyl, $C_1$-$C_7$-alkoxy-$C_1$-$C_7$-alkyl, $C_1$-$C_7$-alkoxy or halo.

Azide refers to a group —N=N$^+$=N$^-$.

Silyl, as used herein, refers to a group according to the formula —SiR11R12R13, wherein R11, R12 and R13 are, independently of each other, $C_1$-$C_7$-alkyl, $C_6$-$C_{10}$-aryl or phenyl-$C_{1-4}$-alkyl. Preferred examples for R11, R12 and R13 are methyl, ethyl, isopropyl, tert-butyl, phenyl or phenyl-$C_{1-4}$-alkyl.

Salts

Salts are especially pharmaceutically acceptable salts or generally salts of any of the intermediates mentioned herein, except if salts are excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

Nitrogen Protecting Groups

The term "nitrogen protecting group" comprises any group which is capable of reversibly protecting a nitrogen functionality, preferably an amine and/or amide functionality. Preferably the nitrogen protecting group is an amine protecting group and/or an amide protecting group. Suitable nitrogen protecting groups are conventionally used e.g. in peptide chemistry and are described e.g. in the relevant chapters of standard reference works such as J. F. W. McOmie, "Protective Groups in Organic Chemistry", Plenum Press, London and New York 1973, in P. G. M. Wuts and T. W. Greene, "Greene's Protective Groups in Organic Synthesis', fourth edition, Wiley, N.J., 2007, and "The Peptides"; volume 3 (editors: E. Gross and J. Meienhofer), Academic Press, London and New York 1981, and "Methoden der organischen Chemie" (Methods of Organic Chemistry), Houben Weyl, fourth edition, volume 15/I, Georg Thieme Verlag, Stuttgart 1974.

Preferred nitrogen protecting groups generally comprise: unsubstituted or substituted $C_1$-$C_6$-alkyl, preferably $C_1$-$C_4$-alkyl, more preferably $C_1$-$C_2$-alkyl, most preferably $C_1$-alkyl, optionally substituted $C_{2-4}$-alkenyl, wherein each $C_1$-$C_5$-alkyl and $C_{2-4}$-alkenyl is optionally mono-, di- or tri-substituted by trialkylsilyl-$C_1$-$C_7$-alkoxy (e.g. trimethylsilylethoxy), cycloalkyl, aryl, preferably phenyl, or a heterocyclic group, preferably pyrrolidinyl, wherein the cycloalkyl group, the aryl ring or the heterocyclic group is unsubstituted or substituted by one or more, e.g. two or three residues, e.g. selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; aryl-$C_1$-$C_2$-alkoxycarbonyl (preferably phenyl-$C_1$-$C_2$-alkoxycarbonyl e.g. benzyloxycarbonyl); $C_1$-$C_{10}$-alkenyloxycarbonyl; $C_{1-6}$-alkylcarbonyl; acetyl or pivaloyl); $C_{6-10}$-arylcarbonyl; $C_1$-$C_6$-alkoxycarbonyl (e.g. tert-butoxycarbonyl); $C_{6-10}$-aryl-$C_{1-6}$-alkoxycarbonyl; allyl or cinnamyl; sulfonyl or sulfenyl; a succinimidyl group, substituted silyl, e.g. triarylsilyl or trialkylsilyl (e.g. triethylsilyl).

Examples of preferred nitrogen protecting groups are acetyl, benzyl, cumyl, benzhydryl, trityl, benzyloxycarbonyl (Cbz), 9-fluorenylmethyloxycarbony (Fmoc), benzyloxymethyl (BOM), pivaloyl-oxy-methyl (POM), trichloroethxoycarbonyl (Troc), 1-adamantyloxycarbonyl (Adoc), allyl, allyloxycarbonyl, trimethylsilyl, tert-butyl-dimethylsilyl (TBDMS), triethylsilyl (TES), triisopropylsilyl (TIPS), trimethylsilyethoxymethyl (SEM), tert-butoxycarbonyl (BOC), tert-butyl, 1-methyl-1,1-dimethylbenzyl, (phenyl) methylbenzene, pyrridinyl and pivaloyl. Most preferred nitrogen protecting groups are acetyl, benzyl, benzyloxycarbonyl (Cbz), triethylsilyl (TES), trimethylsilyethoxymethyl (SEM), tert-butoxycarbonyl (BOC), pyrrolidinylmethyl and pivaloyl.

Examples of more preferred nitrogen protecting groups are, pivaloyl, pyrrolidinylmethyl, t-butoxycarbonyl, benzyl and silyl groups, particularly silyl groups according to the formula SiR11R12R13 group, wherein R11, R12 and R13 are, independently of each other, $C_1$-$C_7$-alkyl, $C_6$-$C_{10}$-aryl or phenyl-$C_1$-$C_4$-alkyl. Preferred examples for R11, R12 and R13 are methyl, ethyl, isopropyl, t-butyl and phenyl. Examples of most preferred nitrogen protecting groups are tert-butoxycarbonyl (BOC), benzoyl, styryl, 1-butenyl, benzyl, p-methoxybenzyl (PMB) and pyrrolidinylmethyl, in particular pivaloyl and tert-butoxycarbonyl (BOC).

In one embodiment the term nitrogen protecting group refers to a group which is selected from the group consisting of $C_1$-$C_6$-alkyl, which is unsubstituted or mono-, di- or tri-substituted by tri-$C_1$-$C_6$-alkylsilyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from N, O, S, S(O) or S(O)$_2$, wherein the aryl ring or the heterocyclic group is unsubstituted or substituted by one, two or three residues, selected from the group consisting of $C_1$-$C_7$-alkyl, hydroxyl, $C_1$-$C_7$-alkoxy, $C_2$-$C_8$-alkanoyl-oxy, halogen, nitro, cyano, and $CF_3$;

$C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl, and silyl, wherein each silyl group is a SiR11R12R13 group, wherein R11, R12 and R13 are, independently of each other, $C_1$-$C_7$-alkyl, $C_6$-$C_{10}$-aryl or phenyl-$C_1$_$C_4$-alkyl.

Generally, in the present application the term "nitrogen protecting group" comprises any group which is capable of reversibly protecting an amino functionality.

If an embodiment requires the removal of the nitrogen protecting group, as defined above, the removal usually can be carried out by using known methods, e.g. as described in the references cited above. Preferably, the nitrogen protecting group, as defined above, is removed by using acidic or basic conditions. Examples for acidic conditions are hydrochloric acid, trifluoroacetic acid, sulphuric acid. Examples of basic conditions are lithium hydroxide, sodium ethoxide. Nucleophiles such as sodium borohydride can be used. In the case of N-benzyl as amino protecting group it can be removed by hydrogenation or by the use of some suitable oxidizing agents, e.g. ceric ammonium nitrate (CAN) or 2,3-dichloro-5,6-dicyano-p-benzoquinone (DDQ). Generally this implies that wherever the term "protecting group" is used in the present specification, a protecting group is only used as such if it is removed for the next to follow product—if it remains, the protecting group is becoming a substituent. Thus, alkyl, such as ethyl, if removed, is a protecting group, if it remains, it becomes a permanent moiety.

Where protecting groups are mentioned, it is their characteristic that, in contrast to groups that remain in a molecule, they are cleaved off in a following reaction step; therefore alkyl, such as ethyl, as protecting group, based on this function, is to be distinguished from alkyl, such as ethyl, that is to stay in a reaction product.

Solvent(s)

Where (appropriate) solvents or solvent mixtures (the term solvent always also refers to single solvents or solvent mixtures of two or more solvents) are mentioned above and in any claims (the appropriate being a dispensable feature), apart from the specific solvents mentioned also one or more solvents from the following group may be used: water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, ketones, such as acetone or methylethylketone, or mixtures of these, for example aqueous solutions, unless otherwise indicated in the description of the processes. Such solvent mixtures may also be used in working up, for example by chromatography or partitioning. Where required or desired, water-free or absolute solvents can be used.

EMBODIMENTS

The following sections describes in more detail, as necessary, the compounds and the individual process steps as laid out in SCHEMES 1 to 5 above.

SECTION A: Novel Intermediates

The present invention provides the following new intermediates:

A compound of formula (1) or a salt thereof,

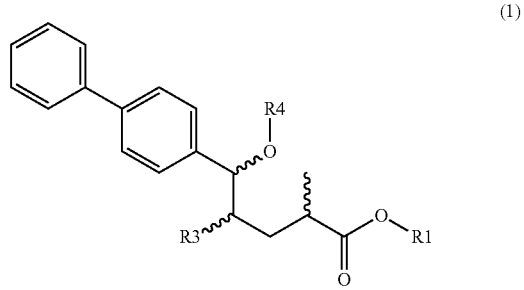

(1)

wherein R1 is hydrogen or $C_1$-$C_6$-alkyl, preferably ethyl,

R3 is —NO$_2$ or —NR'R", wherein R' and R" are independently of each other hydrogen or a nitrogen protecting group, preferably R3 is —NO$_2$ or —NHR' wherein R' is a nitrogen protecting group, preferably tert-butyloxycarbonyl, and R4 is selected from hydrogen, $C_1$-$C_6$-carbonyl, $C_1$-$C_6$-alkoxycarbonyl and a sulphonyl group, preferably hydrogen.

Preferably, the compound (1) or a salt thereof has a configuration according to formula (1-R)

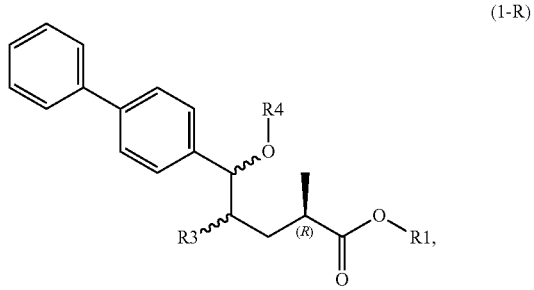

(1-R)

wherein R1, R3 and R4 are as defined for the compound of formula (1).

More preferably, it has a configuration according to formula (1-RS)

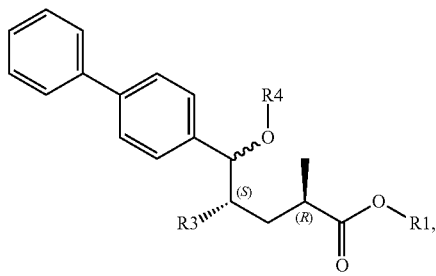
(1-RS)

wherein R1, R3 and R4 are as defined for the compound of formula (1).

In one embodiment thereof, the invention relates to a compound of formula (1-a)

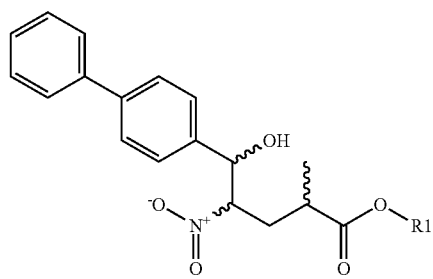
(1-a)

preferably of formula (1-a-R)

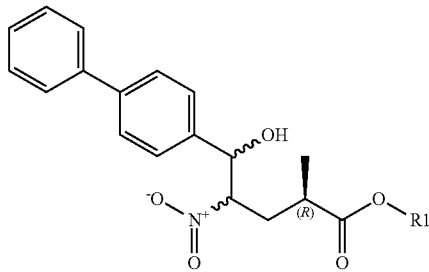
(1-a-R)

wherein R1 is hydrogen or $C_1$-$C_6$-alkyl, preferably ethyl.

In one embodiment thereof, the invention relates to a compound of formula (1-a-RS)

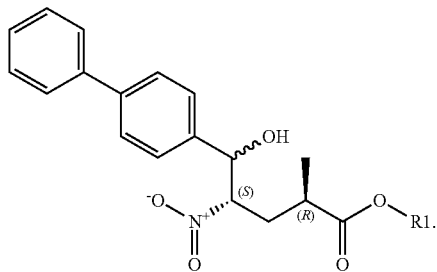
(1-a-RS)

wherein R1 is hydrogen or $C_1$-$C_6$-alkyl, preferably ethyl.

In a further embodiment thereof, the invention relates to a compound selected from the group of the following compounds with configurations according to formulas (1-a-RRR), (1-a-RRS), (1-a-RSR), and (1-a-RSS)

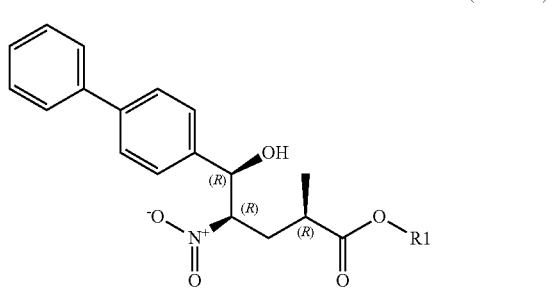
(1-a-RRR)

(1-a-RRS)

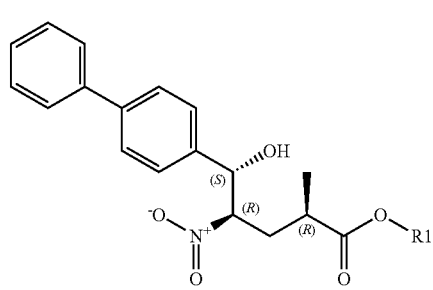
(1-a-RSR)

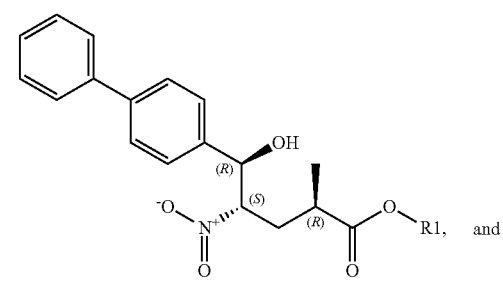
(1-a-RSS)

and

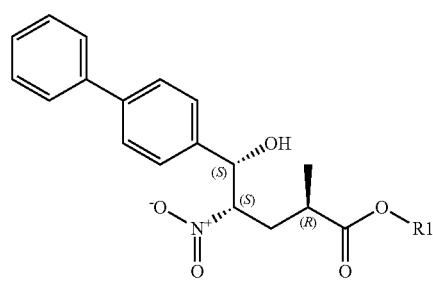

wherein in above formulae R1 is hydrogen or $C_1$-$C_8$-alkyl, preferably ethyl.

In another embodiment, the invention relates to a compound of formula (1-b)

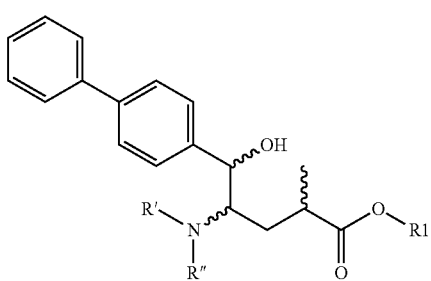
(1-b)

preferably a compound of formula (1-b-R)

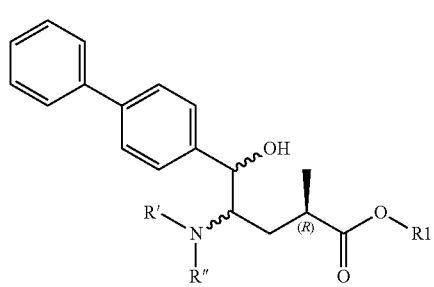
(1-b-R)

wherein in the above formulas R' and R" are independently of each other hydrogen or a nitrogen protecting group, preferably R" is hydrogen and R' is a nitrogen protecting group, preferably tert-butyloxycarbonyl, and wherein R1 is hydrogen or $C_1$-$C_5$-alkyl, preferably ethyl.

In one embodiment thereof, the compound is of formula (1-b-RS)

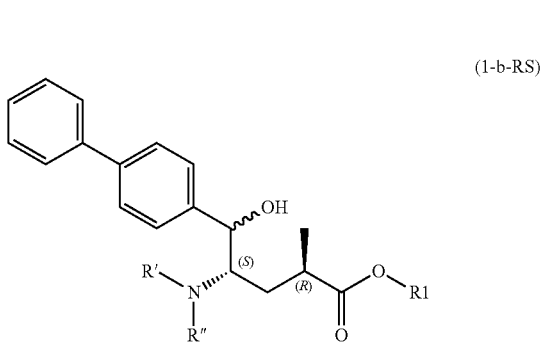
(1-b-RS)

wherein R' and R" and R1 are as defined above.

In a further embodiment, the present invention relates to a compound of formula (1-d)

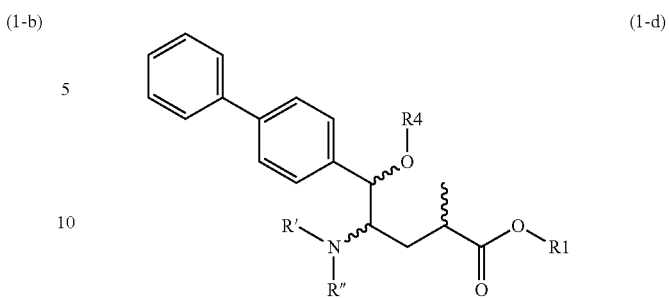
(1-d)

preferably a compound of formula (1-d-R)

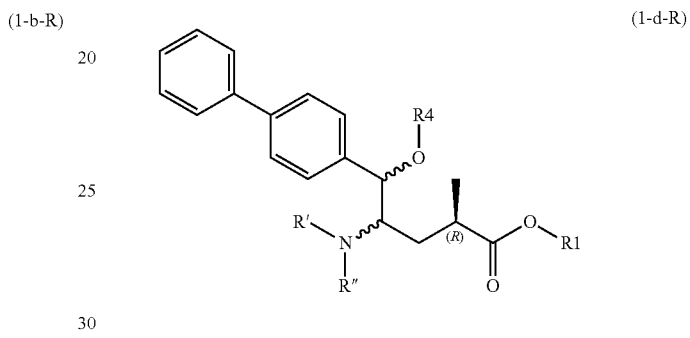
(1-d-R)

wherein in the above formulas R' and R" are independently of each other hydrogen or a nitrogen protecting group, preferably R" is hydrogen and R' is a nitrogen protecting group, preferably tert-butyloxycarbonyl, R1 is hydrogen or $C_1$-$C_6$-alkyl, preferably ethyl, and R4 is an OH-activating group, preferably selected from $C_1$-$C_6$-carbonyl, $C_1$-$C_6$-alkoxycarbonyl and sulphonyl.

In one embodiment thereof, the compound is of formula (1-d-RS)

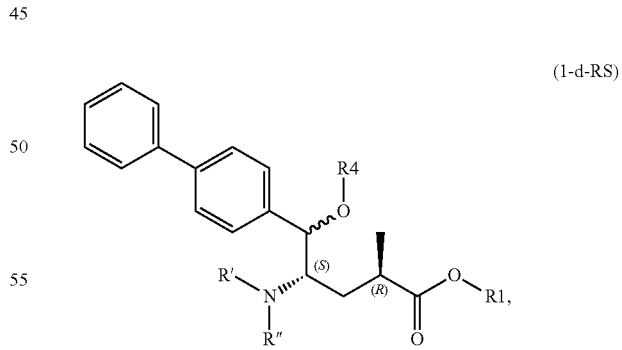
(1-d-RS)

wherein R' and R" and R1 and R4 are as defined above.

In further embodiments, as an example, when R3 is —NHR' and R1 is ethyl, the compound of formula (1) and (1-RS) are represented by the following formulae:

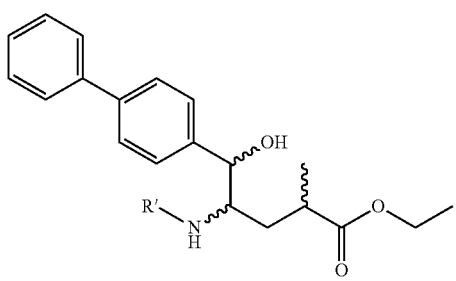

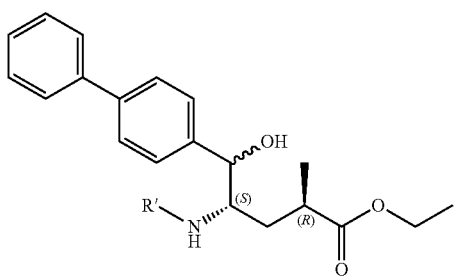

wherein in both formulae, R' is a nitrogen protecting group, preferably tert-butyloxycarbonyl, respectively.

With the preferred nitrogen protecting group, said intermediate compounds are represented by the following formulae (in which the second formula indicating the R,S stereochemistry is the preferred compound):

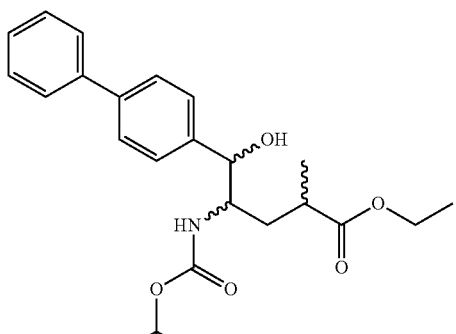

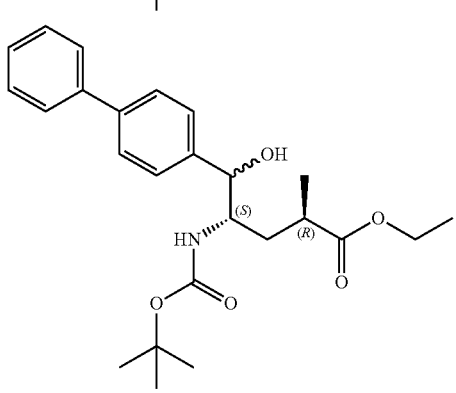

As a further example, when R is —NO₂ the compound of formula (1) or (1-RS) is represented by the following formulae (in which the second formula indicating the R,S stereochemistry is the preferred compound):

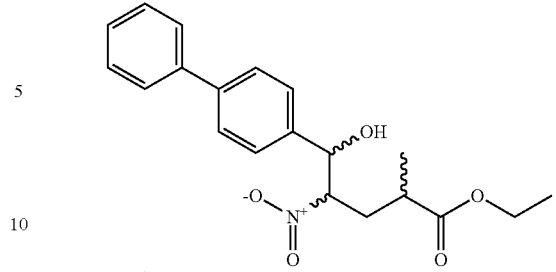

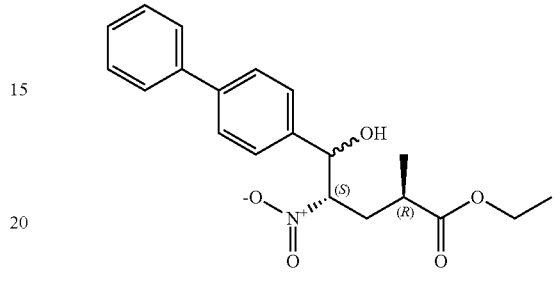

In a separate embodiment, the present invention provides another new intermediate:

A compound of formula (2) or a salt thereof,

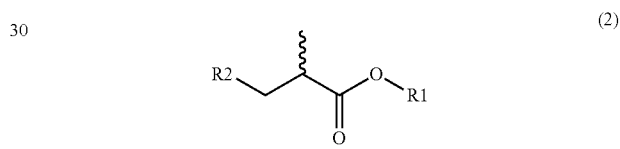

(2)

wherein R1 is hydrogen or ethyl, and R2 is [(E)- or (Z)-formoximyl] —CHNOH, or [nitro-methylene]-CH₂NO₂, preferably R2 is —CH₂NO₂.

Preferably said compound or its salt has a configuration according to formula (2-R),

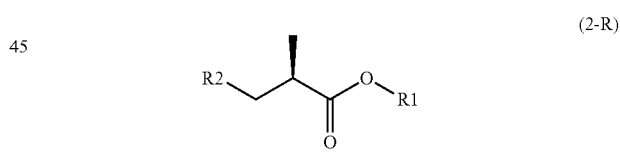

(2-R)

wherein R1 is hydrogen or $C_1$-$C_6$-alkyl, preferably ethyl, and R2 is [(E)- or (Z)-formoximyl] —CHNOH, or [nitro-methylene] —CH₂NO₂, preferably R2 is —CH₂NO₂.

In one embodiment thereof, wherein R2 is nitro-methylene (—CH₂NO₂) or (E)- or (Z)-formoximyl (—CHNOH), the compound of formula (2-R) is represented by the following formulae (2-a-R) and (2-b-R), respectively:

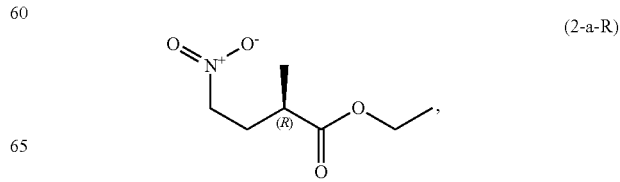

(2-a-R)

-continued (2-b-R)

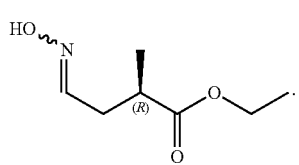

In one embodiment thereof, wherein R1 is ethyl and R2 is nitro-methylene (—CH$_2$NO$_2$) or (E)- or (Z)-formoximyl (—CHNOH), the compound of formula (2-R) is represented by the following formulae (2-a-R-Et) and (2-b-R-Et), respectively:

(2-a-R-Et)

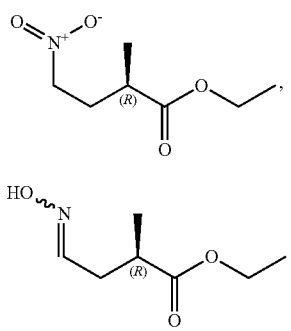

(2-b-R-Et)

A preferred intermediate compound of the present invention is the compound of formula (2), wherein R is —CH$_2$NO$_2$ and R1 is ethyl so that said compound is represented by formula (2-a-R-Et)

(2-a-R-Et)

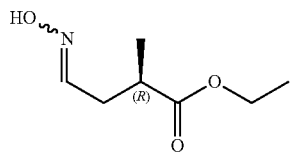

SECTION B: Henry Reaction (SCHEME 2)

In a second aspect, the present invention provides a process (Nitro aldol reaction, Henry reaction) for producing the compound of formula (1-a)

(1-a)

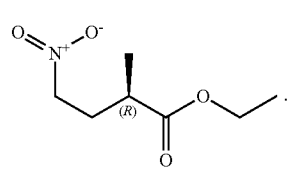

wherein R1 is hydrogen or C$_1$-C$_6$-alkyl, preferably ethyl, preferably of formula (1-a-R)

(1-a-R)

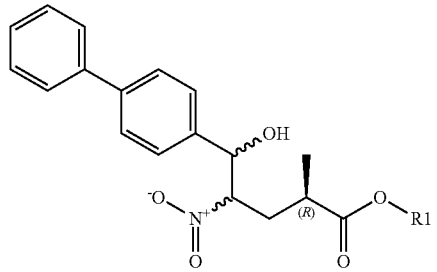

wherein R1 is hydrogen or C$_1$-C$_6$-alkyl, preferably ethyl, more preferably wherein the compound of formula (1-a-R) is of formula (1-a-R-Et)

(1-a-R-Et)

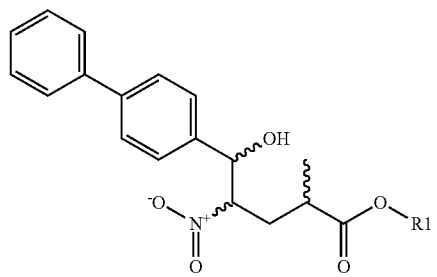

comprising reacting a compound of formula (2-a)

(2-a)

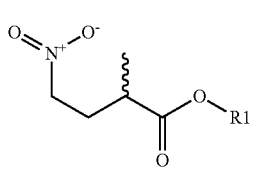

wherein R1 is hydrogen or C$_1$-C$_6$-alkyl, preferably ethyl, preferably wherein the compound of formula (2-a) is of formula (2-a-R)

(2-a-R)

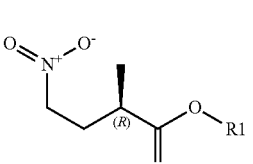

wherein R1 is hydrogen or C$_1$-C$_6$-alkyl, preferably ethyl, more preferably wherein the compound of formula (2-a-R) is of formula (2-a-R-Et)

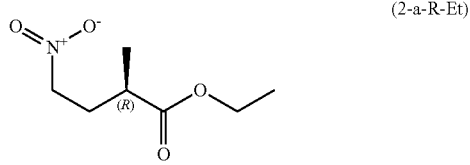

(2-a-R-Et)

with the aldehyde compound of formula (3)

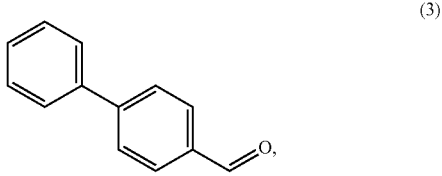 [SMILES: O=Cc1ccc(-c2ccccc2)cc1]

(3)

wherein the reaction of compound of formula (2-a), (2-a-R), or (2-a-R-Et), with the compound of formula (3) is performed in the presence of a catalyst.

In one embodiment thereof, the produced compound of formula (1-a-R) is of the configuration according to formula (1-a-RS)

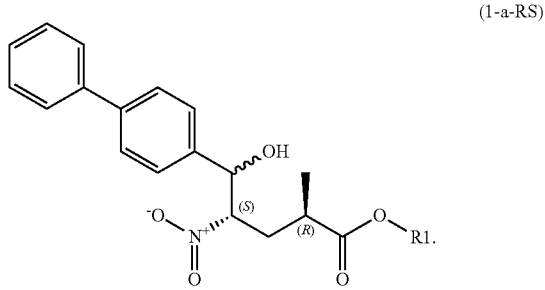

(1-a-RS)

The possible catalysts for the Henry reactions can be found in three major groups.

First are the metal complex catalysts which are comprising or consisting of a central metal atom and different chiral ligands. There a many chiral ligands in the literature derived from 1,1'-Bi-2-naphthol (BINOL), Bis(oxazoline) derivatives (BOX/PyBOX/IndaBOX), Cinchona alkaloids, Diphenylethylenediamine (DPEN), trans 1,2-diaminocyclohexane (DAC), Salen, oxazolidine and other chiral precursors. Together with the metal (Zn, Co, Cu, Cr, Fe) they form a metal complex with the ability to catalyse the desired reaction as well as the induction of chirality into the products.

Second are the organocatalysts which are mostly based on Cinchona alkaloid, guanidine or activated nitroalkanes (nitronate).

Last is the biocatalytic approach which uses either whole cells or enzymes for the Henry reaction.

Examples of said different types of catalysts are described N. Ananthi, S. Velmathi, Indian J. Chem. 2013, 52, 87-108; S. E. Milner, T. S. Moody, A. R. Maguire, Eur. J. Org. Chem. 2012, 3059-3067; G. Chelucci, Coord. Chem. Rev. 257, 2013, 1887-1932; C. Palomo, M. Oiarbide, A. Laso, Eur. J. Org. Chem., 2007, 2561-2574; G. Blay, V. Hernandez-Olmos, J. R. Pedro, Synlett, 2011, No. 9, 1195-1211; F. A. Luzzio, Tetrahedron, 2001, 57, 915-945; J. Boruwa, N. Gogoi, P. P. Saikia, N. C. Barua, Tetrahedron: Asymmetry, 2006, 17, 3315-3326 and are incorporated herein by reference.

Catalysts that are commercially available are used according to a preferred embodiment of the invention, see for example in the following table:

Table "Commercially Available Ligands"

TABLE

"Commercially Available Ligands"

| Ligand | Source |
| --- | --- |
| BINOL | Sigma-Aldrich |
| DAC | Sigma-Aldrich |
| DPEN | Sigma-Aldrich |
| BOX | Sigma-Aldrich |
| PyBOX | Sigma-Aldrich |
| IndaBOX | Sigma-Aldrich |
| Salen | Sigma-Aldrich |
| amino-acid-derived | not found, best remove |
| Cinchona alkaloids | Sigma-Aldrich |

Preferably, catalysts from the group of metal complex catalyst are used for this second aspect of the present invention.

In a more preferred embodiment, the process of the second aspect of the present invention as described herein is an asymmetric Henry reaction and provides the compound of formula (1-a-R) in a configuration according to formula (1-a-RS)

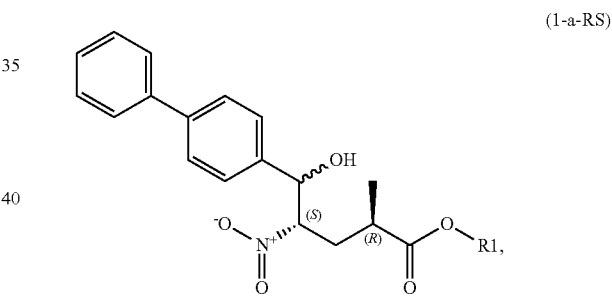

(1-a-RS)

wherein the reaction of compound of formula (2-a-R) with the compound of formula (3) is performed in the presence of a chiral catalyst.

Preferably said chiral catalyst is selected from the group of metal complex catalysts comprising a metal and a chiral ligand, preferably said metal is a transition metal, more preferably said metal is selected from the group of Zn, Co, Cu, Cr, and Fe, and said chiral ligand is selected from the group of 1,1'-bi-2-naphthol (BINOL) ligands, diaminocyclohexan (DAC) ligands (e.g. trans 1,2-DAC), diphenylethylenediamin (DPEN) ligands, camphor-pyridine ligands, bis-oxazoline (BOX) ligands, ligands comprising a pyridine ring flanked by two oxazoline groups (PyBOX), IndaBOX ligands, Salen ligands, amino acid derived ligands (e.g. ligands made from L-valine or L-proline), ligands derived from natural products (e.g. cinchona alkaloid derivatives, sparteine derivatives, camphor-pyridine derivatives), and mixtures thereof. In preferred invention embodiments, the commercially available ligands mentioned above in the table "Commercially Available Ligands" are used. Preferred chiral ligands are camphor-pyridine derived ligands, DAC ligands and DPEN ligands.

In one embodiment thereof, the catalyst is a metal complex catalysts comprising a metal and a chiral ligand, wherein the metal is Cu and the chiral ligand is selected from the groups of camphor-pyridine ligands, DAC ligands and DPEN ligands.

Particularly preferred are DAC ligands, more particularly preferred are asymmetric DAC ligands, even more particularly preferred is the compound of formula (4a)

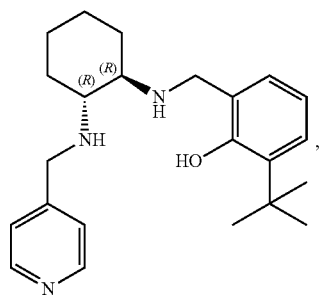
(4a)

which is herein also referred to as "Woggon ligand" (Adv. Synth. Catal. 2011, 353, 1797-1806).

More particularly preferred and also an embodiment of the invention is the compound of formula (4b)

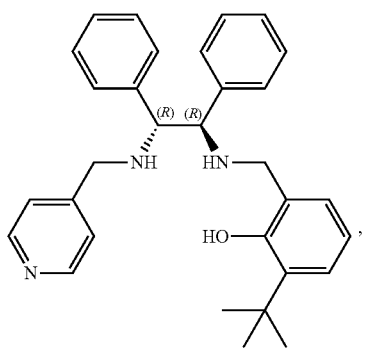
(4b)

which is herein also referred to as "Sedel ligand".

In one embodiment thereof of the second aspect of the invention, it is provided a process wherein the compound of formula (2-a) has a configuration according to formula (2-a-R)

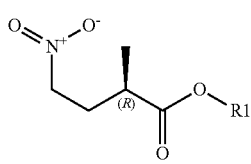
(2-a-R)

and wherein the compound according to formula (1-a-R) is produced as a mixture of compounds with configurations according to formulae (1-a-RS) and (1-a-RR)

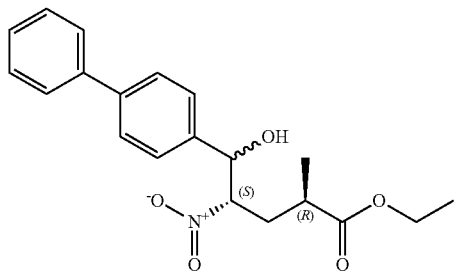
(1-a-RS)

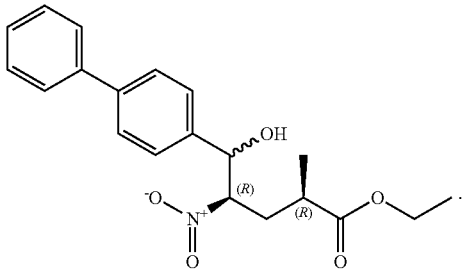
(1-a-RR)

Preferably said compound with configuration according to formula (1-a-RS) is present in the mixture to at least 50%, more preferably to at least 60%, yet more preferably to at least 63%, most preferably to at least 65%.

This diastereomeric (or any enantiomeric) purity mentioned herein can be measured e.g. by chiral HPLC or other customary analytical methods known in the art, e.g. as described hereinbelow or in the examples.

In another embodiment according to the second aspect of the present invention, the invention provides a process wherein the compound of formula (2-a) has a configuration according to formula (2-a-R)

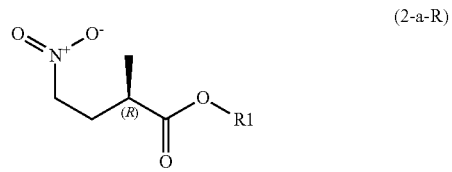
(2-a-R)

and wherein the compound according to formula (1-a-R) is produced as a mixture consisting of one, two, three or four compounds selected from the group of the following compounds with configurations according to formulas (1-a-RRR), (1-a-RRS), (1-a-RSR), and (1-a-RSS)

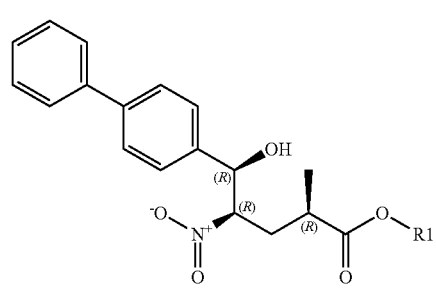
(1-a-RRR)

(1-a-RRS)

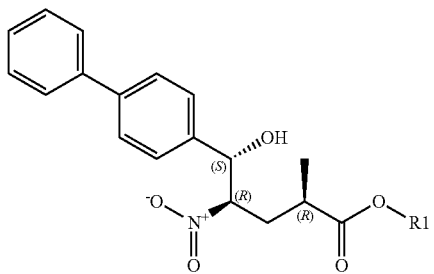

(1-a-RSR)

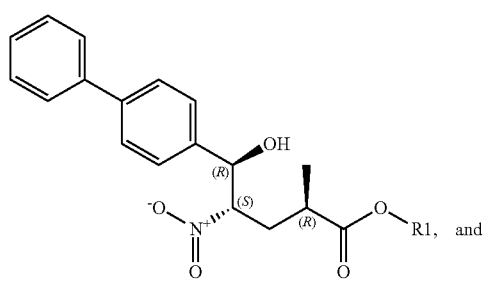

(1-a-RSS)

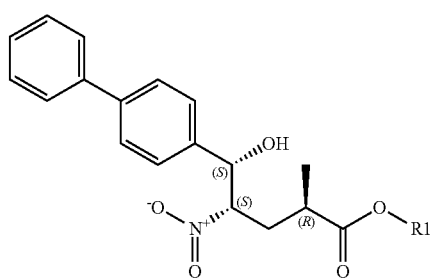

wherein in above formulaes R1 is hydrogen or $C_1$-$C_6$-alkyl, preferably ethyl.

Preferably, the compound with a configuration according to formula (1-a-RSR) is present in the mixture to at least 50%, preferably to at least 60%, more preferably to at least 63% and yet more preferably to at least 65%.

More particularly, there is provided the process according to the second aspect of the present invention, wherein the catalyst is a metal complex catalyst comprising a metal and a chiral ligand metal and the metal is Cu and the chiral ligand is camphor-pyridine and/or compound of formula (4a), preferably the the metal is Cu and the chiral ligand is compound of formula (4a or 4b).

More specifically, there is provided the process according to the second aspect of the present invention, wherein the catalyst is a metal complex catalysts comprising copper(II) acetate [Cu(OAc)$_2$] in an amount of 5-20 mol %, preferably 8-12 mol %, and compound of formula (4a), the Woggon ligand, in an amount of 8-23 mol %, more preferably 13-17 mol % based on the total number of molecules of compound of formula (2-a).

More specifically, there is provided the process according to the second aspect of the present invention, wherein the catalyst is a metal complex catalysts comprising copper(II) acetate [Cu(OAc)$_2$] in an amount of 5-20 mol %, preferably 8-12 mol %, and compound of formula (4b), the Sedel ligand, in an amount of 5-20 mol %, more preferably 10-14 mol % based on the total number of molecules of compound of formula (2-a).

As solvent for the process according to the second aspect polar protic solvents (e.g. methanol, ethanol, propanol, butanol), polar aprotic solvents (e.g. tetrahydrofuran (THF), dimethylformamide (DMF), dichloromethane (DCM), acetonitrile (ACN)), or apolar aprotic solvent (e.g. toluene) may be used. Alternatively, mixtures of two or more of those solvents/solvent groups or ionic liquids may be used. Preferably, polar solvents are used. More preferably, polar aprotic solvents are used to achieve high yields. A particularly preferred solvent in this regard is THF. All solvents containing aldehydes, ketones or nitro groups (e.g. acetone, nitromethane) must not be used for the second aspect of the present invention as those solvents are not inert.

To increase the reaction rate and to further improve stereochemical selectivity, a base may be added to as further process agent in the process according to the second aspect. Suitable bases are e.g. 1,8-diazabicycloundec-7-ene (DBU), 1,4-diazabicyclo[2.2.2]octane (DABCO), N,N-Diisopropylethylamine (DIPEA), triethylamine (Et$_3$N), (−)-spartein. A preferred base is DBU to ensure high conversion rates and high stereochemical selectivities.

Preferred combinations of ligand/base are DAC/DBU, DPEN ligands/DBU, camphor-pyridine ligands/DABCO as those combinations provide high conversion rates and high selectivity. Particularly preferred in this regard is the combination Woggon ligand/DBU.

Preferred combinations of ligand/base are DPEN ligands/DBU or camphor-pyridine ligands/DABCO, as those combinations provide high conversion rates and high selectivity. Particularly preferred in this regard is the combination Sedel ligand/DBU.

To avoid side reactions, low temperatures are preferred. Low temperatures according to the present invention are temperatures around or below 0° C., preferably 0 to −78° C., more preferably −15 to −50° C., even more preferably, −25 to −45° C., even more preferably −45±5° C.

In a preferred embodiment, the process according to the second aspect of the present invention is performed in the presence of DBU in THF at −45±5° C.

In an even more preferred embodiment the process according to the second aspect of the present invention is performed in presence of copper(II) acetate [Cu(OAc)$_2$] in an amount of 8-12 mol %, and compound of formula (4), the Woggon ligand, 13-17 mol % based on the total number of molecules of compound of formula (2-a), and DBU as base in THF as solvent and at temperatures of −45±5° C.

In an even more preferred embodiment the process according to the second aspect of the present invention is performed in presence of copper(II) acetate [Cu(OAc)$_2$] in an amount of 8-12 mol %, and compound of formula (4a), the Sedel ligand, 10-14 mol % based on the total number of molecules of compound of formula (2-a), and DBU as base in THF as solvent and at temperatures of −45±5° C.

SECTION C: Oxime Oxidation (SCHEME 3A, Last Step)

In a further invention embodiment, especially as an element of the process according to the second aspect of the present invention, there is provided a process wherein the compound of formula (2-a),

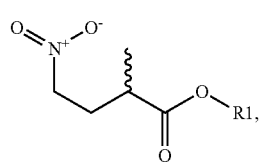

(2-a)

preferably the compound of formula (2-a-R)

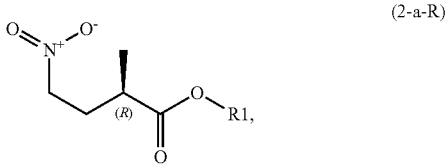

is prepared by oxidation of a compound of formula (2-b)

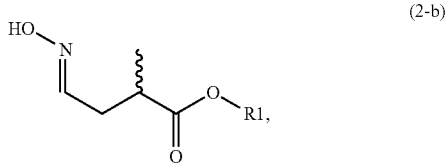

preferably a compound of formula (2-b-R)

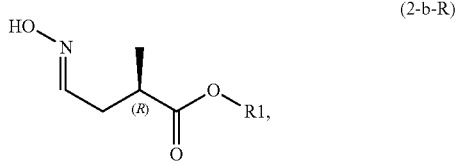

wherein in above formulae R1 is hydrogen or $C_1$-$C_6$-alkyl, preferably ethyl,
said oxidation comprising the use of one or more oxidants and optionally a catalyst, preferably said oxidant is hydrogen peroxide—urea (also referred to as urea hydrogen peroxide (UHP)), and preferably a catalyst is used and said catalyst is comprising tungsten (W), more preferably said catalyst is a tungstate, even more preferably said catalyst is sodium tungstate.

As oxidants, especially urea hydrogen peroxide (UHP), sodium perborate (SPB) and sodium percarbonate (SPC), Oxone® (potassium peroxymonosulfate), Mo(IV) oxodiperoxo complex [BzOMoO($O_2$)$_2$]—$^tBu_4N^+$ (Benz-Mo), peracetic acid (PAA), performic acid (PFA), pertrifluoroacetic acid (PTFA), or peroxyacetimidic acid are used, preferably UHP is used.

More specifically, UHP is used in an amount of 2 to 4, preferably 3 equivalents in relation to 1 equivalent of compound of formula (2-b-R).

To decrease the reaction time, a catalyst may be used. As catalyst, especially sodium tungstate, methyl trioxo rhenium (MTO), or magnesium monoperoxyphthalate hexahydrate (MMPP) is used. Preferably, sodium tungstate is used. More preferably, sodium tungstate dihydrate is used. More specifically, sodium tungstate dihydrate is used in an amount of 0.3 to 0.7, preferably 0.5 equivalent in relation to 1 equivalent of compound of formula (2-b-R).

The reaction is preferably performed at elevated temperatures, preferably at 30-80° C., more preferably at 40-60° C., even more at 50±5° C.

To increase reaction and conversion rate the reaction is preferably conducted at 40-60° C., preferably at 50±5° C. and the amount of UHP may be increased up to 2-4 equivalent, preferably 3 equivalent.

As solvent a polar solvent is preferably used. More preferably, a protic polar solvent is used. Yet more preferably, methanol is used as solvent.

In a preferred embodiment the process is performed with UHP as oxidant in an amount of 2 to 4, preferably 3 equivalents, and with sodium tungstate dihydrate as catalyst in an amount of 0.3 to 0.7, preferably 0.5 equivalent, in relation to 1 equivalent of compound of formula (2-b-R), and at 30-80° C., more preferably at 40-60° C., even more at 50±5° C., in a polar solvent, preferably a protic polar solvent, more preferably in methanol.

SECTION D: Oxime Formation (SCHEME 3A, Second Step)

There is further provided, as further invention embodiment, the process, especially as a step of the process according to the second aspect of the present invention, wherein the compound of formula (2-b)

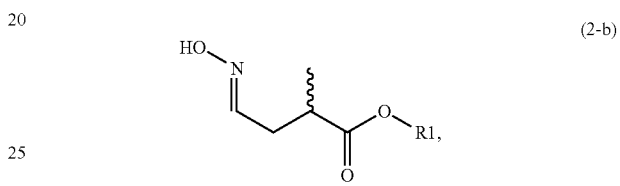

preferably the compound of formula (2-b-R)

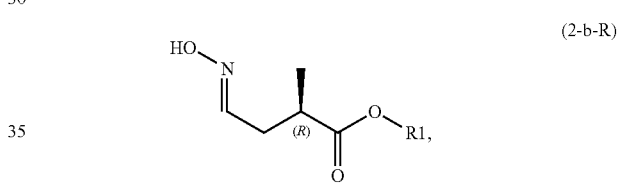

wherein in above formulae R1 is hydrogen or $C_1$-$C_6$-alkyl, preferably ethyl,
is prepared by oxime formation of a compound of formula (2-c)

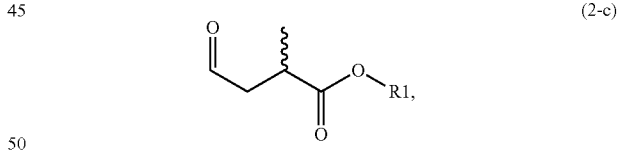

preferably a compound of formula (2-c-R)

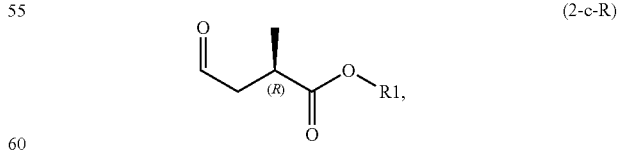

wherein in above formulae R1 is hydrogen or $C_1$-$C_6$-alkyl, preferably ethyl,
said oxime formation preferably comprising the use of hydroxylamine or a salt thereof.

As hydroxylamine source, hydroxylamine in water (50%), or hydroxylamine salts ($H_2NOH$)$_2H_2SO_4$ or H₂NOH.HCl is preferably used. More preferably, hydroxylamine in water (e.g. 50%) is used.

The hydroxylamine is used in an amount which is a minimum 10% excess to compound of formula (2-c-R), preferably it is used in 10% excess to compound of formula (2-c-R).

As solvent a polar solvent is used, preferably an aprotic polar solvent is used, more preferably acetonitrile is used as solvent.

The process is preferably performed at ambient temperatures (e.g. 15-30° C.).

In a preferred embodiment the process is performed hydroxylamine in water (50%) in 10% excess to compound of formula (2-c-R) in a polar solvent is used, preferably an aprotic polar solvent is used, more preferably acetonitrile at ambient temperatures.

SECTION E: Hydroformylation (SCHEME 3A, First Step)

There is further provided, as further invention embodiment, in particular as a step proceeding the Oxime formation of Section D, a process, especially as a part of the process according to the second aspect of the present invention, wherein the compound of formula (2-c)

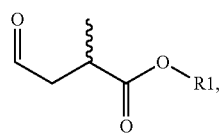
(2-c)

preferably the compound of formula (2-c-R)

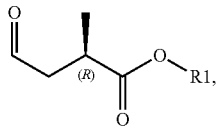
(2-c-R)

is prepared by hydroformylation, preferably asymmetric hydroformylation of a methacrylate of formula (2-d)

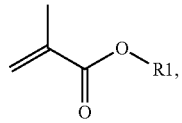
(2-d)

wherein in above formulae R1 is hydrogen or $C_1$-$C_6$-alkyl, preferably ethyl (i.e. the compounds are methacrylate or $C_1$-$C_6$-alkyl methacrylate, preferably, ethyl methacrylate); said hydroformylation comprising the use of carbon monoxide (CO), hydrogen ($H_2$) and optionally a metal complex catalyst.

In one embodiment, said metal complex catalyst comprises platinum (Pt), rhodium (Rh), or tin (Sn), or combinations thereof in combination with chiral ligands. Preferred metal/chiral ligand combinations are (R,R)-(+)-1,2-Bis(t-butyl-methyl-phosphino)benzene ((R,R)-BenzP*) in combination with Rh or (S,S)-(+)-2,3-O-Isopropylidene-2,3-dihydroxy-1,4-bis(diphenylphosphino)butane (S,S-DIOP) in combination with Sn/Pt. More preferably said catalyst is PtCl(SnCl₃)[(S,S)-DIOP].

The process is especially performed in an autoclave reactor under pressure, preferably a Hastelloy autoclave reactor, preferably at an pressure equivalent to 40 bar of CO/$H_2$ in 300

The ethyl methacrylate is preferably dissolved in a non-polar solvent; more preferably it is dissolved in toluene.

The ratio between CO and $H_2$ is preferably from 1:2 to 2:1, preferably the ratio is 1:1.

The process is preferably performed at elevated temperatures, more preferably at 50-100° C., yet more preferably at 70±10° C.

Said elevated temperatures are preferably applied for a total of 50-100 h, more preferably for 50-100 h, yet more preferably for 70±10 h.

In a preferred embodiment the process is performed using the catalyst PtCl(SnCl₃)[(S,S)-DIOP] in an autoclave reactor under pressure, for example a Hastelloy autoclave reactor, preferably at an pressure equivalent to 40 bar of CH/$H_2$ in 300 mL, whereas the ethyl methacrylate is dissolved in a non-polar solvent; preferably it is dissolved in toluene and the ratio between CO and $H_2$ is from 1:2 to 2:1, preferably the ratio is 1:1 and an elevated temperatures, preferably at 50-100° C., more preferably at 70±10° C. is applied especially for a total of 50-100 h, preferably for 70±10 h.

SECTION F (SCHEME 3B and SCHEME 4) (Alternative to SECTIONS C-E Above)

There is further, as alternative to the process above for obtaining the compound of the formula (2-a), provided a process, especially as a part of the process according to the second aspect of the present invention, wherein the compound of formula (2-a),

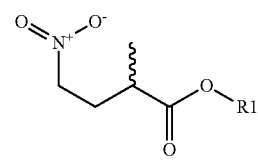
(2-a)

is prepared by treating a compound of formula (2-d)

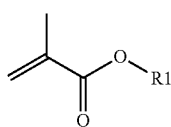
(2-d)

with nitromethane, preferably in the presence of bases selected from DBU, CsF/nBu4NCl, and tetramethyl guanidine, most preferably tetramethyl guanidine, optionally followed by a chiral separation of the compound of formula (2-a) to obtain the compound of formula (2-a-R)

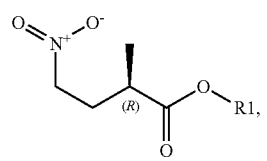
(2-a-R)

wherein in above formulae R1 is hydrogen or $C_1$-$C_6$-alkyl, preferably ethyl, In one embodiment, the chiral separation is performed by chiral crystallization (from solutions, dispersions or emulsions) or by chiral (especially simulated moving bed (SMB)) chromatography, preferably said chiral separation is carried out by chiral simulated moving bed (SMB) chromatography.

The chiral crystallization is performed by firstly saponificating of the compound (2-a) with a strong base, preferably potassium hydroxide (KOH), secondly performing the chiral crystallization in the presence of a chiral amine, preferably cinchonidium salts or (S)-(–)-alpha-methylbenzylamine, most preferably (S)-(–)-alpha-methylbenzylamine, and finally and optionally performing the esterification with the corresponding $C_1$-$C_6$-alkyl alcohol, preferably ethanol, preferably in the presence of p-toluene sulphonic acid.

The chiral SMB chromatography is performed by using an SMB unit (e.g. Bayer CC50 SMB) equipped with chiral HPLC columns (e.g. Chiralpak ID 20 um 8×(100×50 mm). Preferably, the compound of formula (2-a) is fed to the system at a concentration of 5-15 g/L, more preferably ca. 10 g/L, in a solvent mixture comprising n-heptane, t-butylmethylether, and a small amount (less than 10%), more preferably in a solvent mixture of methanol n-heptane/t-butylmethylether/methanol in the ratio 65/34/1. Flow rates are as the following: for eluent 20-30 L/h, for feed 0.25-0.75 L/h, for extract 3-8 L/h, for raffinate 1-3 L/h, for recycle 15-20 Uh. The switch time is set to 50-100 seconds, preferably 70-75 sec.

SECTION G: Nitro Hydrogenation (SCHEME 1)

According to the second aspect of the present invention there is provided, especially subsequent to the process according to the second aspect of the invention, but also independently as a separate embodiment, a process for producing a compound of formula (1-b)

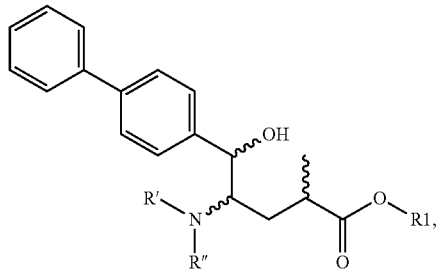

(1-b)

preferably a compound of formula (1-b-R),

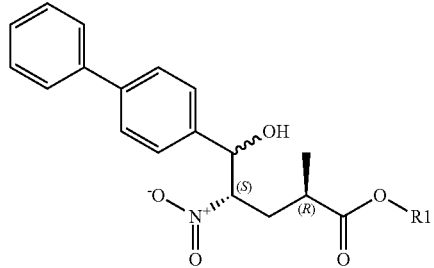

(1-b-R)

comprising hydrogenation of a compound of formula (1-a)

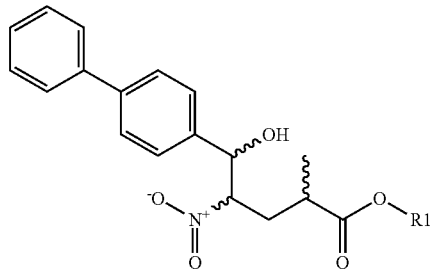

(1-a)

preferably a compound of formula (1-a-R)

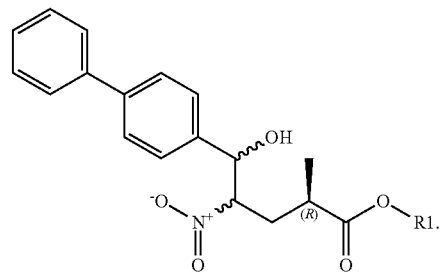

(1-a-R)

optionally in the presence of a nitrogen protecting agent, preferably di-tert-butyl dicarbonate, wherein in the above formulae R' and R" are independently of each other hydrogen or a nitrogen protecting group, preferably R" is hydrogen and R' is a nitrogen protecting group, preferably tert-butyloxycarbonyl, and wherein wherein R1 is hydrogen or $C_1$-$C_5$-alkyl, preferably ethyl.

In one embodiment of this process the compound of formula (1-a-R) is of formula (1-a-RS)

(1-a-RS)

and the compound of formula (1-b-R) is of formula (1-b-RS)

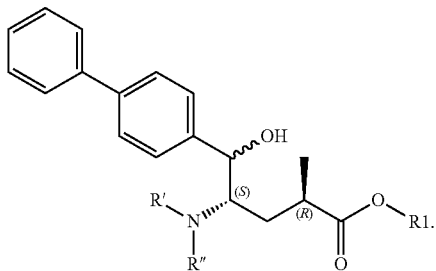

(1-b-RS)

In both cases, R1, R' and R" are as defined for the compound of the formula (1-b).

In one embodiment thereof, there is provided a process for producing a compound of formula (1-b-R)

(1-b-R)

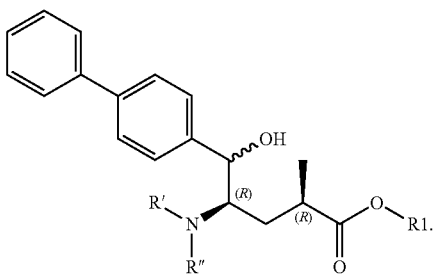

wherein R' and R" are independently of each other hydrogen or a nitrogen protecting group, preferably R" is hydrogen and R' is a nitrogen protecting group, preferably tert-butyloxycarbonyl, and wherein wherein R1 is hydrogen or $C_1$-$C_8$-alkyl, preferably ethyl, and wherein said compound of formula (1-b-R) is a mixture of compounds with configurations according to formulae (1-b-RR) and (1-b-RS)

(1-b-RR)

(1-b-RS)

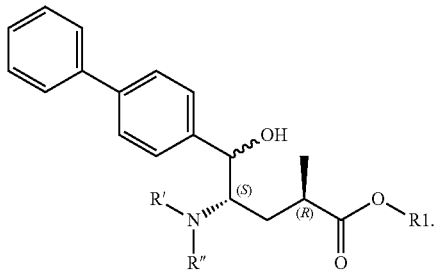

wherein said compound with configuration according to formula (1-b-RS) is present in the mixture to at least 60%, more preferably to at least 63%, even more preferably to at least 65%.

In said embodiment, the process comprises hydrogenating a mixture of compounds with configurations according to formulae (1-a-RR) and (1-a-RS)

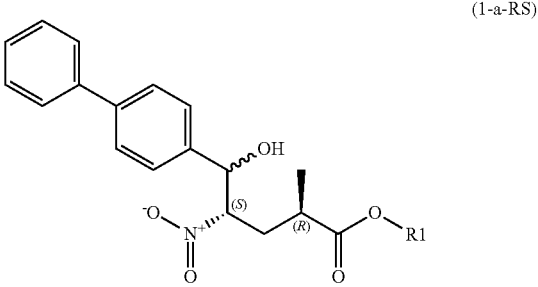

(1-a-RS)

(1-a-RR)

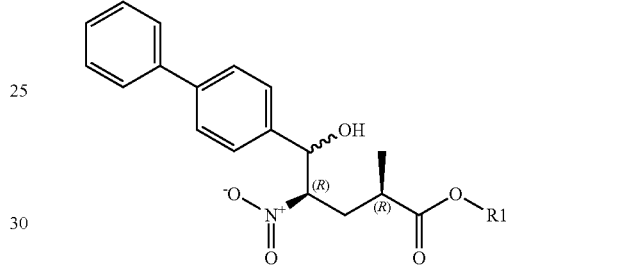

wherein the compound with configuration according to formula (1-a-RS) is present in said mixture to at least 60%, preferably to at least 63%, more preferably to at least 65%, and the use of a nitrogen protecting agent, preferably di-tert-butyl dicarbonate ($Boc_2O$).

R1, R' and R" are as defined for the compound of the formula (1-b).

In one embodiment thereof, the hydrogenation comprises the use of a metal catalyst, preferably a metal catalyst comprising a metal selected from the group of nickel, palladium or platinum, more preferably Raney nickel, even more preferably Raney nickel type 3202.

The process is preferably performed in a hydrogenation reactor. Preferably the catalyst is applied to this process as 50% water slurry.

The nitrogen protecting group introducing agent, especially $Boc_2O$, is used for this process preferably in molar excess over sum of molar amount of compounds of formulae (1-a-RS) and (1-a-RR), preferably in an excess of 20-100%, more preferably in an excess of 50±10%.

The process is preferably performed with pressurized hydrogen, for example the hydrogen is pressurized up to 4 bar.

The process is preferably performed at elevated temperatures, more preferably from 30-70° C., yet more preferably from 35-50° C., even more preferably from 40-45° C.

The elevated temperatures is preferably applied for 2 to 24 h, preferably for 5-15 h, more preferably for 10±2 h.

In a preferred embodiment the process is performed with Raney nickel as 50% water slurry, using $Boc_2O$ in excess over sum of compounds of formulae (1-a-RS) and (1-a-RR), preferably in an excess of 20-100%, more preferably in an excess of 50±10%, using pressurized hydrogen, preferably using hydrogen pressurized up to 4 bar, at elevated temperatures, preferably from 30-70° C., more preferably from 35-50° C., even more preferably from 40-45° C. for 2 to 24 h, preferably for 5-15 h, more preferably for 10±2 h.

In one specific embodiment of the present aspect of the invention, in this process of SECTION G, the compound of formula (1-a) is produced by a process as set out in section B above.

SECTION H: Reduction (SCHEME 1)

According to the fourth aspect of the present invention there is provided, especially subsequent to the process mentioned under Section F, a process for producing a compound of formula (6)

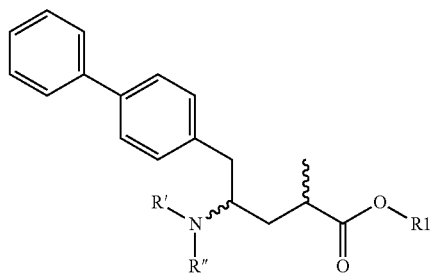

(6)

wherein R' and R" are independently of each other hydrogen or a nitrogen protecting group, preferably R' and R" are both hydrogen, and R1 is hydrogen or $C_1$-$C_6$-alkyl, preferably ethyl, preferably a compound of formula (6-R)

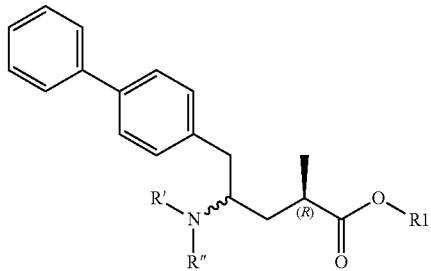

(6-R)

said process comprising
taking a compound of formula (1-b)

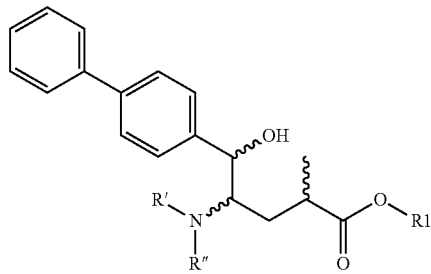

(1-b)

wherein R' and R" are independently of each other hydrogen or a nitrogen protecting group, preferably R" is hydrogen and R' is a nitrogen protecting, preferably group tert-butyloxycarbonyl, and R1 is hydrogen or $C_1$-$C_6$-alkyl, preferably ethyl, preferably a compound of formula (1-b-R)

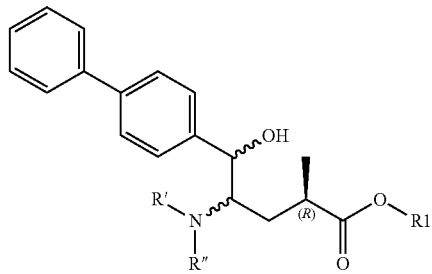

(1-b-R)

optionally treating the compound of formula (1-b) with an OH-activating agent to obtain a compound of formula (1-d)

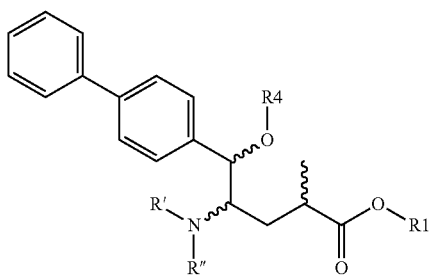

(1-d)

wherein R' and R" are independently of each other hydrogen or a nitrogen protecting group, preferably R" is hydrogen and R' is a nitrogen protecting group, preferably tert-butyloxycarbonyl, R1 is hydrogen or $C_1$-$C_6$-alkyl, preferably ethyl, and R4 is an OH-activating group, preferably selected from $C_1$-$C_6$-carbonyl, $C_1$-$C_8$-alkoxycarbonyl and sulphonyl;

preferably a compound of formula (1-d-R)

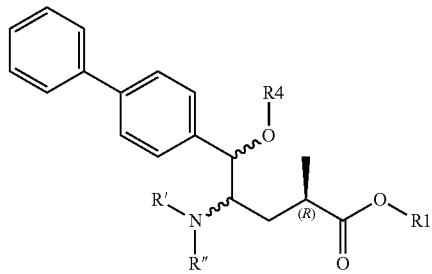

(1-d-R)

and subjecting the compound of formula (1-d)

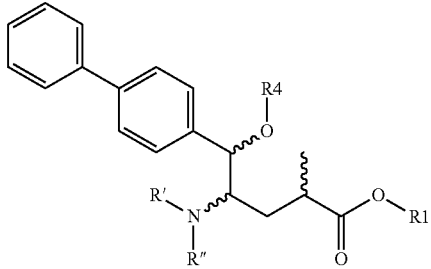
(1-d)

wherein R' and R" are independently of each other hydrogen or a nitrogen protecting group, preferably R" is hydrogen and R' is a nitrogen protecting group, preferably ten-butyloxycarbonyl, R1 is hydrogen or $C_1$-$C_6$-alkyl, preferably ethyl, and R4 is hydrogen or a OH-activating group, preferably selected from $C_1$-$C_6$-carbonyl, $C_1$-$C_6$-alkoxycarbonyl and sulphonyl, preferably a compound of formula (1-d-R)

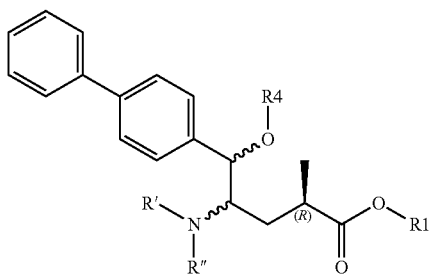
(1-d-R)

to a hydrogenation reaction to obtain the compound of formula (6), preferably of formula (6-R).

An OH-activating agent herein is any reagent which can convert a hydroxyl group into a leaving group. Examples of suitable OH-activating agents are acylating agents transforming the alcohol into an ester, or acylating agents, transforming the alcohol into a carbonate, such as chloroformate, e.g. methyl chloroformate in combination with magnesium or lithium alkylates, e.g. lithium tert-amylate, or sulphonating agents, such as methanesulfonyl- or toluenesulfonyl halides, for example methanesulfonylchloride or toluenesulfonylchloride, transforming the alcohol into an sulphonate.

In one embodiment, the OH-activating agent is selected from $C_1$-$C_6$-alkyl chloroformate, optionally substituted $C_1$-$C_6$-alkyl-sulfonyl halide and optionally substituted $C_6$-$C_{10}$-arylsulfonyl halides.

In one embodiment of the above process, the compound of formula (1-b-R) is of formula (1-b-RS)

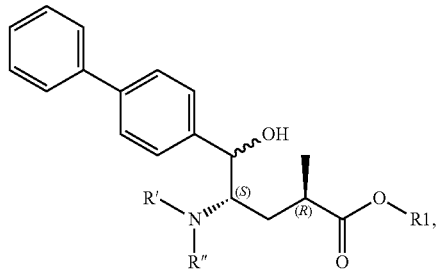
(1-b-RS)

the compound of formula (1-d-R) is of formula (1-d-RS)

(1-d-RS)

and the compound of formula (6-R) is of formula (6-RS)

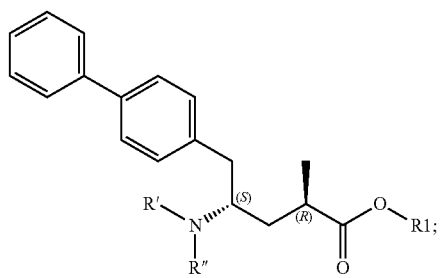
(6-RS)

wherein R1, R4, R' and R" are as defined for the respective compounds above.

In one embodiment of this process, the hydrogenation of a compound of formula (1-d) or (1-b) is carried out in the presence of a catalyst, preferably a transition metal catalyst selected from Pt, Pd, or Rh, preferably on carbon, more preferably the transition metal catalyst is Pd on carbon (Pd/C).

In the embodiments of this aspect, the OH group activation is performed preferably with methylchloroformate as an OH-activating agent, in the presence of a base, preferably lithium tert-amylate and the subsequent hydrogenation, and the hydrogenation reaction is performed in the presence of a metal catalyst, preferably said metal catalyst comprises palladium, even more preferably, the hydrogenation is performed with pressurized hydrogen in the presence of palladium on charcoal.

Both reaction steps, the OH-activation as well as the hydrogenation, are preferably performed in polar aprotic solvents, more preferably in isopropyl acetate. Preferably, water is added for the hydrogenation step.

The OH-activation is preferably performed at cool temperatures for several minutes to several hours (h) reaction time duration, preferably in the range of −20 to 10° C. for 30 min to 5 h, more preferably −5 to 5° C. for 2-4 h, even more preferably 0-2° C. for 3 h. The hydrogenation is preferably performed at elevated temperatures and under pressure for several hours (h) up to a few days, more preferably in the range of 40-89° C. and 2-20 bar for 5 to 36 h, even more preferably 70-80° C. and 8-13 bar for 16 to 24 h, even more preferably at about 75° C. and about 11 bar for about 20 h.

Preferably the hydrogenation catalyst is palladium on charcoal, more preferably, palladium 5% on charcoal, 50% water-wet. Preferably the catalyst is of type 437.

Most preferably, the OH-activation is performed in isopropylacetate at 0-2° C. for 3 h and the hydrogenation is performed in isopropyl acetate/water at 75° C. for 20 h with palladium 5% on charcoal, type 457, 50% water-wet.

In another embodiment of the present invention, the compound of formula (1-b) or the compound of formula (1-d), wherein R4 is hydrogen, when used in the process of the present SECTION H is produced by a process according to the process in SECTION G.

In further embodiment, there is provided a process as described before, wherein the hydrogenation reaction in step B) to obtain a compound of formula (6)

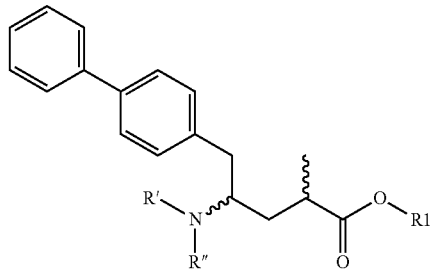

(6)

wherein R' and R" are independently of each other hydrogen or a nitrogen protecting group, preferably R' and R" are both hydrogen, and R1 is hydrogen or $C_1$-$C_6$-alkyl, preferably ethyl,
preferably a compound of formula (6-R)

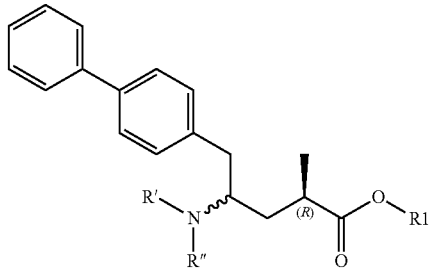

(6-R)

is carried out via the intermediate compound of formula (7) wherein R1, R' and R" are as defined for the compound of the formula (6),

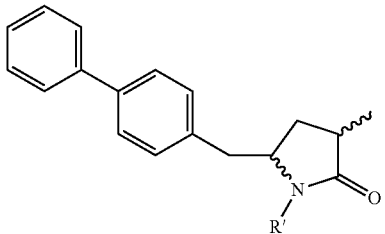

(7)

wherein R' is hydrogen or a nitrogen protecting group, preferably hydrogen or tert-butyloxycarbonyl,
preferably via the intermediate compound of formula (7-R)

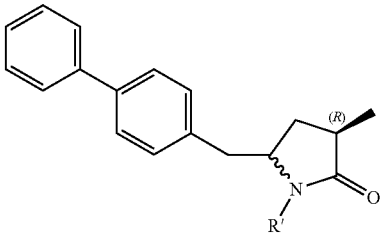

(7-R)

with R' as just defined; which compound is reacted with a ring opening agent, preferably comprising water and/or a $C_1$-$C_6$-alkanol, to obtain a compound of formula (6).

The lactam ring opening reaction can occur under basic, neutral or acidic conditions. Examples for ring opening agents are nucleophilic bases such as alkali metal hydroxides (for example sodium hydroxide or lithium hydroxide) or neutral compounds such as metal alkoxides (such as sodium ethoxide). Further examples are Lewis or Brønsted acids, preferably in the presence of water. Preferred acids are mineral acids such as sulphuric, perchloric and hydrochloric acid. Sulphonic acids such as para-toluenesulphonic acid are also suitable as are polymer-bound acids such as Amberlyst®. Especially hydrochloric acid is used as a ring opening agent.

The ring opening agent is used catalytically or stoichiometrically. Preferably, the ring opening agent is used in an amount from 1 to 10 equivalents.

The ring opening reaction is performed within a wide temperature range, e.g. between −10° C. and +150° C. Preferably, the reaction is carried out between +20° C. and +125° C. The reaction is preferably carried out in a variety of solvents e.g. water, or ethanol or mixtures of these. Additional solvents such as toluene, isopropyl acetate, tetrahydrofuran or tert-butylmethylether can be used, preferably, ethanol and/or water is used.

The reaction from compound (1-d), or salt thereof, to compound (6), or salt thereof, is preferably carried out according to various embodiments. For example, a compound according to formula (1-d), or salt thereof, wherein R' is hydrogen can be used as starting material, or a compound according to formula (6), or salt thereof, wherein R' is a nitrogen protecting group, as defined above, preferably a pivaloyl group or a BOC group. If a compound according to formula (1-d), or salt thereof, wherein R' is a nitrogen protecting group, as defined above, is used as starting material, preferably the nitrogen protecting group is removed during the ring opening reaction. This means that preferably a compound according to formula (6), or salt thereof, wherein R' is hydrogen, is obtained.

Even more preferably in said process the compound of formula (6-R) is of formula (6-RS)

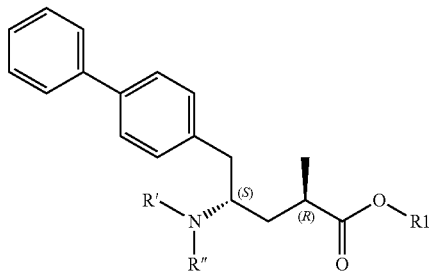

(6-RS)

wherein R' and R" are independently of each other hydrogen or a nitrogen protecting group, preferably R" is hydrogen and R' is a nitrogen protecting group, preferably tert-butyloxycarbonyl, R1 is hydrogen or $C_1$-$C_6$-alkyl, preferably ethyl; and the compound of formula (7-R) is of formula (7-RS)

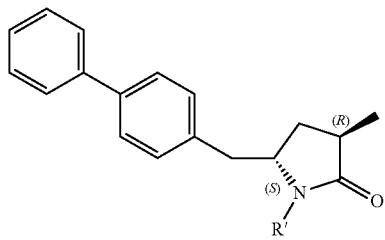

(7-RS)

wherein R' is hydrogen or a nitrogen protecting group, preferably tert-butyloxycarbonyl.

In another embodiment, there is provided a process as described before, wherein the obtained compound of formula (6)

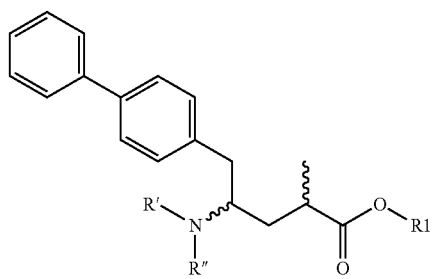

(6)

wherein R' and R" are independently of each other hydrogen or a nitrogen protecting group, preferably R' and R" are both hydrogen, and R1 is hydrogen or $C_1$-$C_6$-alkyl, preferably ethyl, preferably the compound of formula (6-R)

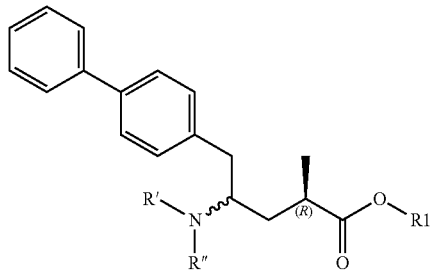

(6-R)

is further reacted to a compound of formula (8)

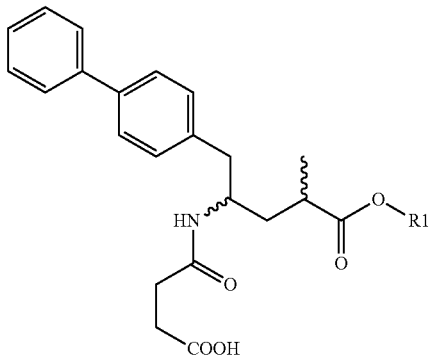

(8)

wherein R1 is hydrogen or $C_1$-$C_6$-alkyl, preferably ethyl, preferably to a compound of formula (8-R)

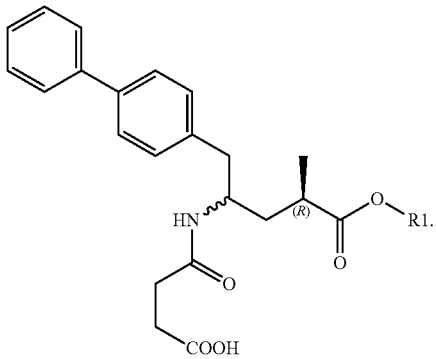

(8-R)

In one embodiment thereof, in said process the compound of formula (6-R) is of formula (6-RS)

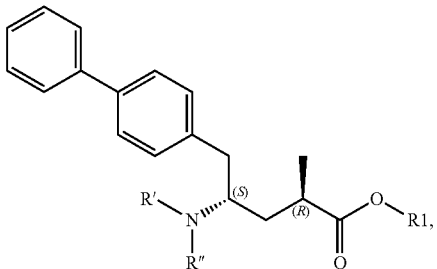

(6-RS)

wherein R' and R" are independently of each other hydrogen or a nitrogen protecting group, preferably R" is hydrogen and R' is a nitrogen protecting group, preferably tert-butyloxycarbonyl, and R1 is hydrogen or $C_1$-$C_6$-alkyl, preferably ethyl, and the compound of formula (8-R) is of formula (8-RS)

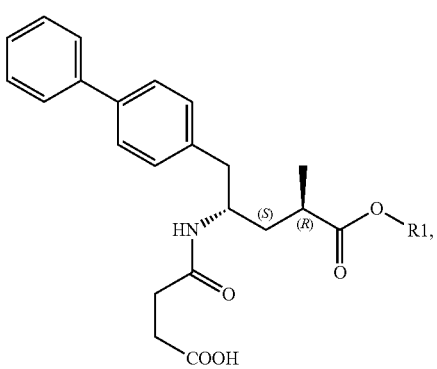

(8-RS)

wherein R1 is hydrogen or $C_1$-$C_5$-alkyl, preferably ethyl (this then refers to sacubitril).

SECTION I: Use of Novel Intermediates

According to the third aspect of the present invention there is provided the use of a compound of formula (1)

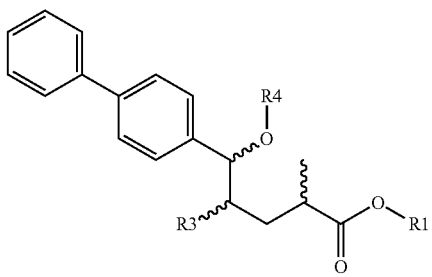

(1)

wherein R1 is hydrogen or $C_1$-$C_5$-alkyl, preferably ethyl,

R3 is —NR'R", or —NO$_2$ and R' and R" are independently of each other hydrogen or a nitrogen protecting group, preferably R3 is —NHR' and R' is tert-butyloxycarbonyl, and R4 is selected from hydrogen, $C_1$-$C_5$-carbonyl, $C_1$-$C_5$-alkoxycarbonyl and a sulphonyl group, preferably hydrogen, in the preparation of a compound of formula (8)

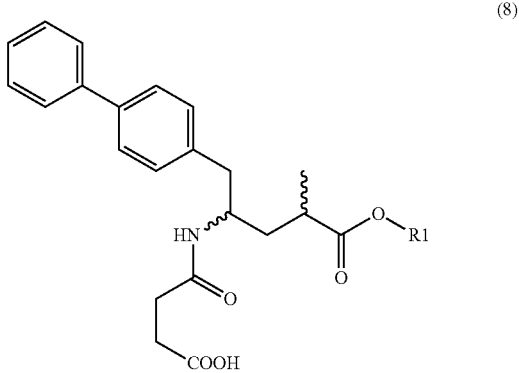

(8)

wherein R1 is hydrogen or $C_1$-$C_6$-alkyl, preferably ethyl, preferably in the preparation of N-(3-carboxyl-1-oxopropyl)-(4S)-(p-phenylphenylmethyl)-4-amino-(2R)-methyl butanoic acid, or salts thereof, or N-(3-carboxyl-1-oxopropyl)-(4S)-(p-phenylphenylmethyl)-4-amino-(2R)-methyl butanoic acid ethyl ester or salts thereof.

This can be done according to processes known in the art, e.g. as described in the following or in analogy thereto: Example 5 in WO 2008/083967 shows the formation of the free acid HCl salt of the compound of the formula (6-R) wherein R1 is hydrogen, and each of R' and R" is hydrogen from (3R,5S)-5-biphenyl-4-ylmethyl-3-methylpyrrolidin-2-one (compound of the formula (7-R) wherein R' is hydrogen):

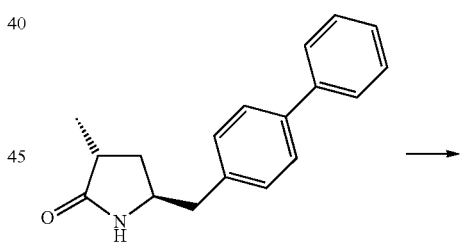

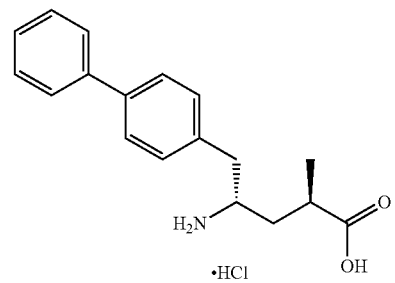

(The compound on the right hand side in the preceding scheme falls under formula (6-RS) wherein each of R', R" and R1 is hydrogen, in the form of the HCl salt.)

Example 8 in WO 2008/083967 shows the further reaction to an N-protected form:

| 51 | 52 |
|---|---|
| 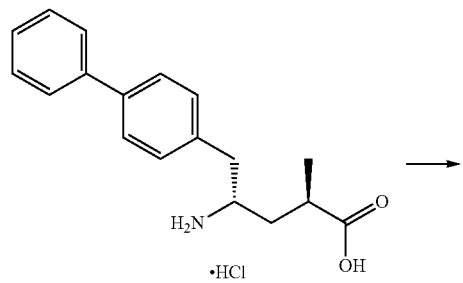 | 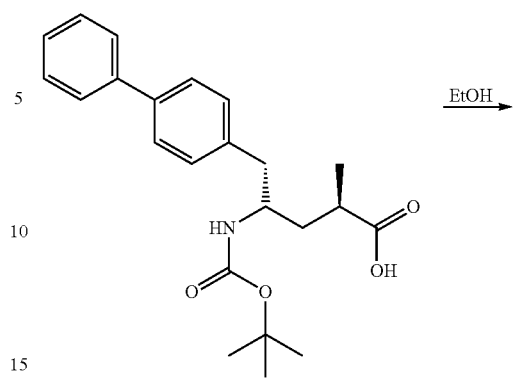 EtOH → |
Example 9-1 in WO 2008/083967 shows formation of the free ethyl ester with thionyl chloride
Scheme 5 (page 40) in WO 2008/083967 for the generic variant, leads from the ethyl ester falling under formula (6-RS wherein each of R' and R" is hydrogen and R1 is ethyl) to the calcium salt of sacubitril:
Scheme 5
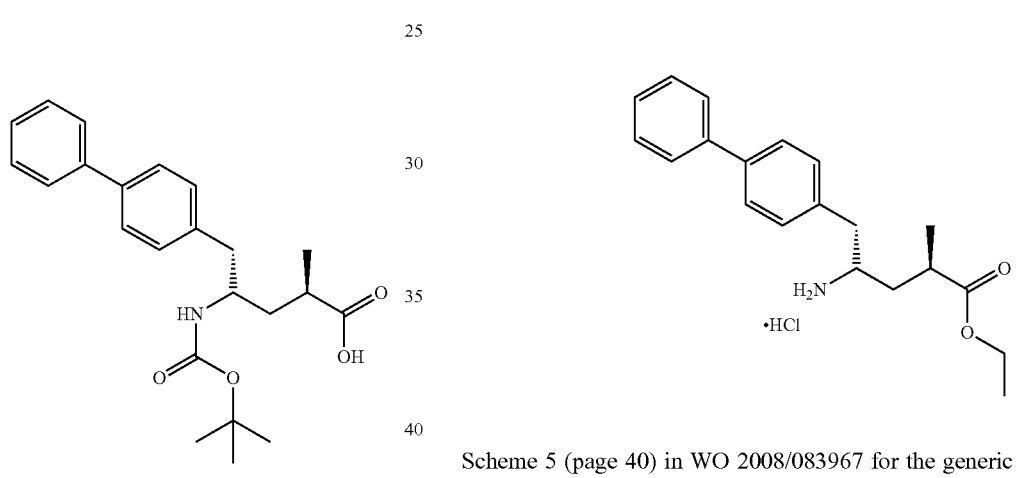
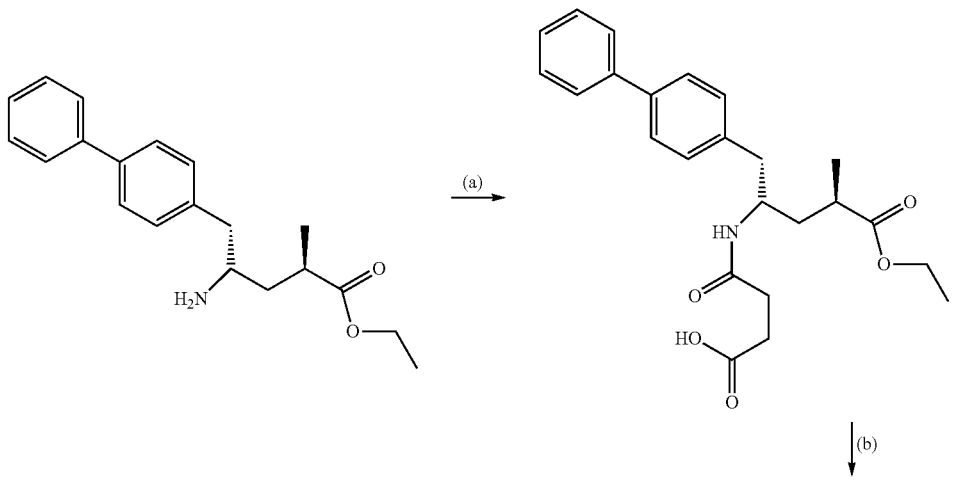

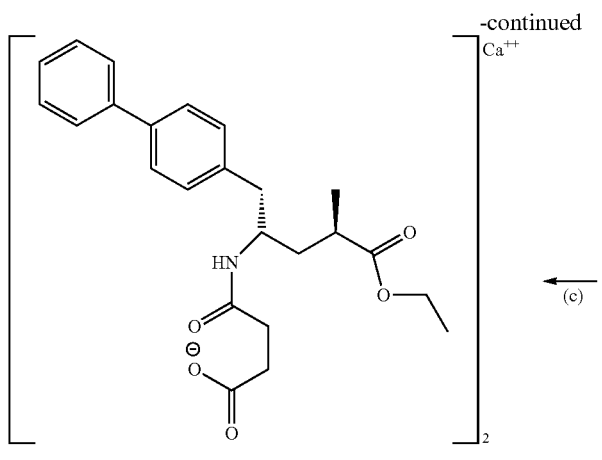

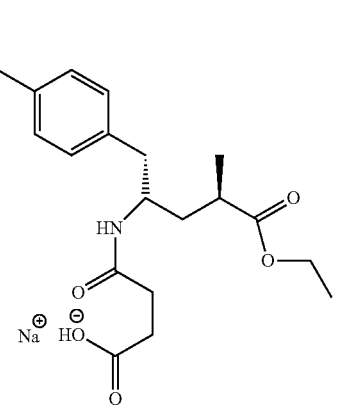

Example 9-2 in WO 2008/083967 provides a way of crystallization of the amino-ethylester.

Example 1 in U.S. Pat. No. 5,217,996 shows the manufacture as in step (a) in the scheme above and in Example 4 the direct formation of the sodium salt.

Alternatively, sacubitril can for example be formed according to the following reaction scheme, according to processes known in the art, from the compound falling under formula (6-RS) in which each of R' and R" is hydrogen and R1 is ethyl the given on the left hand side in the following scheme to the compound falling under formula (8-R) wherein R1 is ethyl given on the right hand side of the following scheme (which is AHU377=sacubitril):

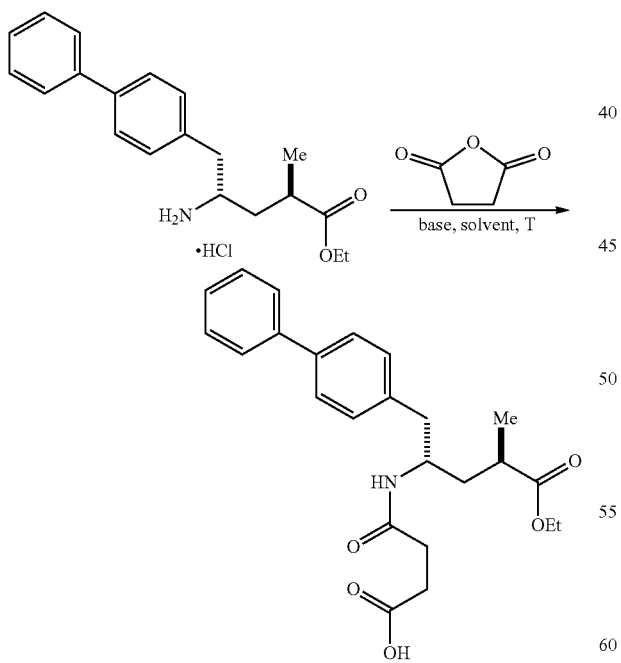

In particular, Example 13 on pages 123 and 124 of WO 2008/083967 describes the link between the non-acivated lactam (not activates as imide) with the free base of the compound given on the left hand side of the preceding reaction scheme and its lactame precursor:

Example 13: (2-a, R1=H) to (3-a, R1=R2=H, R3=Et)

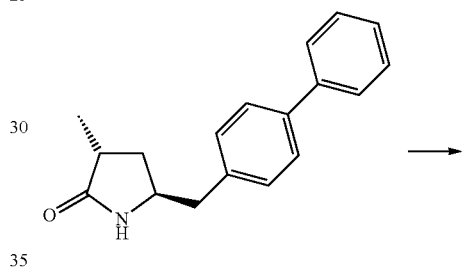

(X=halo, especially Cl).

These and other known processes are particular examples for a manufacture of sacubitril or a salt thereof, and thus represent a variant for those parts of the invention where the manufacture of sacubitril or related compounds is envisioned or mentioned. Therefore the use of a compound of the formula (6-RS) disclosed herein for the manufacture of sacubitril is clearly amenable to the person skilled in the art.

Another embodiment provides the use of the compound of formula (1-a-R)

(1-a-R)

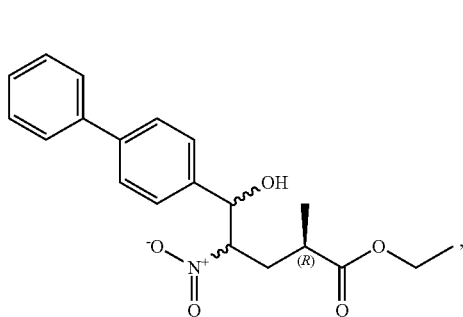

said compound preferably being a mixture of compounds with configurations according to formulae (1-a-RS) and (1-a-RR)

(1-a-RS)

(1-a-RR)

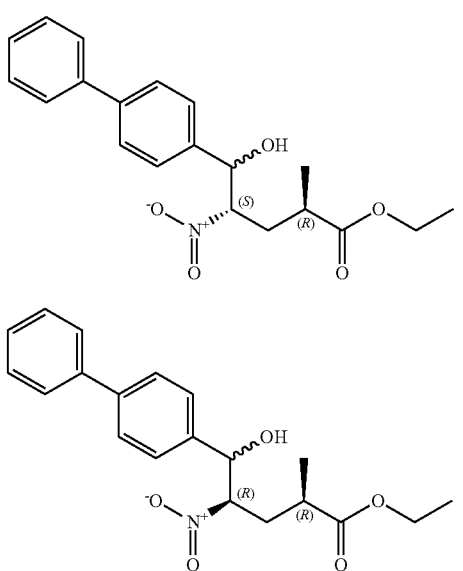

wherein the compound with configuration according to formula (1-a-RS) is present in the mixture to at least 60%, preferably to at least 63%, more preferably to at least 65%, in the preparation of NEP-inhibitors, particularly in the preparation of sacubitril (N-(3-carboxyl-1-oxopropyl)-(4S)-(p-phenylphenylmethyl)-4-amino-(2R)-methyl butanoic acid), or salts thereof.

There is further provided, as invention embodiment, the use of compound of formula (7-R—H)

(7-R-H)

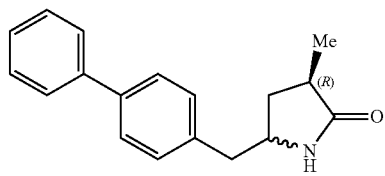

wherein said compound (7-R—H) is a mixture of the the stereomers 3R5S and 3R5R and wherein the stereoisomer 3R5S of formula (7-RS—H)

(7-RS-H)

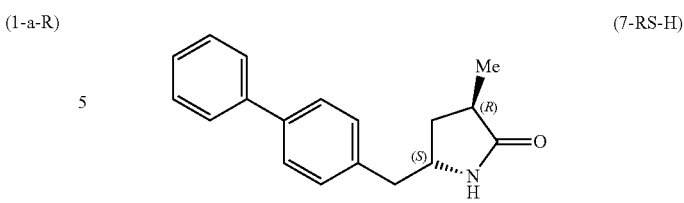

is present in the mixture to at least 60%, preferably to at least 63%, more preferably to at least 65%, in the preparation of NEP-inhibitors, particularly in the preparation of the NEP inhibitor prodrug N-(3-carboxyl-1-oxopropyl)-(4S)-(p-phenylphenylmethyl)-4-amino-(2R)-methyl butanoic acid ethyl ester according to formula (A) (also known in the art as sacubitril), or salts thereof:

(A)

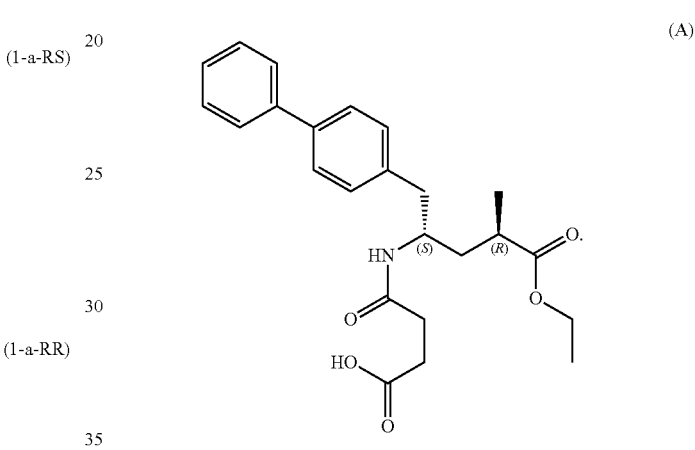

The process for producing said butanoic acid ethyl ester based on compound (7-RS—H) is described in WO2008/083967 (e.g. on pages 37-40). The process for producing a complex of sacubitril together with valsartan is described in WO2007/056546. Said complex is useful in the treatment of cardiovascular diseases.

SECTION H: Sedel Ligand

According to the first aspect of the present invention there is also provided the compound of formula (4b) which is herein also referred to as "Sedel ligand", (4b)

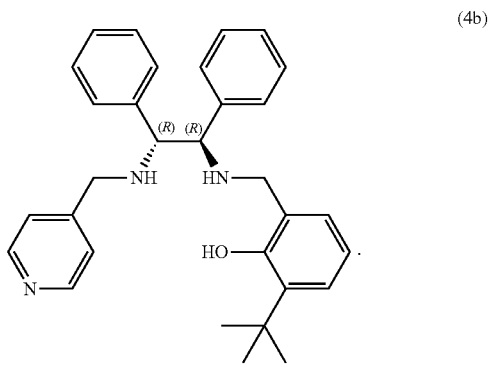

Said Sedel ligand is also referred to as 2-(tert-butyl)-6-((((1R,2R)-1,2-diphenyl-2-((pyridin-4-ylmethyl)amino)ethyl)amino)methyl)phenol or as 2-tert-Butyl-6-({(1R,2R)-1,2-diphenyl-2-[(pyridin-4-ylmethyl)-amino]-ethylamino}- methyl)-phenol. Said Sedel ligand is an asymmetric chiral N,N,O-ligand which is suitable to form together with a transition metal, preferably Cu, a complex which acts as catalyst for an asymmetric (stereoselective Henry reaction of a nitro compound with an aldehyde compound by which a new C—C bond is generated. Said Sedel ligand is used preferably in an amount of 0.1-20 mol %, together with 0.1-20 mol % of a transition metal, preferably Cu(OAc)$_2$, and optionally but preferably ca. 1-20 mol % 1,8-diazabicyclo[5.4.0]undec-7-ene (DBU), in a non-protic but polar organic solvent, preferably THF, at cool temperatures, preferably below 0° C., more preferably at ca. −20° C. to −50° C.

EXAMPLES

Hereinafter, the present invention is described in more details and specifically with reference to the examples, which serve to illustrate, however, are not intended to limit the scope of the present invention.

Example 1: Ethyl (2R)-2-methyl-4-oxobutanoate (Compound 2-c-R-Et) from Ethyl Methacrylate

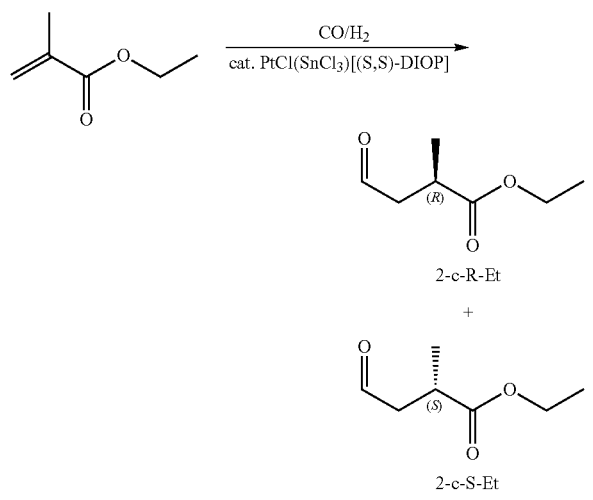

In a 300 ml Hastelloy autoclave was placed ethyl methacrylate (5.72 g, 50.0 mmol), toluene (60 ml) and PtCl(SnCl$_3$)[(S,S)-DIOP] catalyst (cf. preparation of the catalyst from dichlorobis(benzonitrile)platinium(II) (ABCR) and (+)-1,4-bis(diphenylphosphin)-1,4 (aka (S,S)-DIOP (Fluka) and tin(II)chloride (Acros) according to: Journal of Organometallic Chemistry, 296, 281-290, 1985) (0.24 g, 0.5 mol %) under argon atmosphere. After flushing the autoclave three times with CO/H$_2$ 1:1, a pressure of 40 bar CO/H$_2$ 1:1 was adjusted at ambient temperature and the reaction was then heated to 70° C. for a total of 70 h. After 30 h at 70° C. the pressure was decreased to 11 bar, the reaction mix was cooled to ambient temperature for IPC analysis, after which the pressure was adjusted one more time to 40 bar and the reaction mix was stirred for another 40 h at 70° C. The mixture was then rotary distilled at a temperature below 50° C., 50 mbar to remove the solvent, and the resulting residue then distilled at 50° C., 0.3 mbar to provide 2.42 g of compound (2-c-Et) as a mixture enriched with the R-enantiomer (2-c-R-Et) as a liquid (total yield with mixture of isomers 33%).

$\delta_H$ (400 MHz, CDCl$_3$) 1.24 (6H), 2.53 (1H), 2.86-3.02 (2H), 4.12-4.19 (2H), 9.78 (1H)

Chiral GC (FID), 12.98 min & 13.26 min (R:S=64:36, 29% ee); Column CP-ChiraSil Dex CB 25×0.25; 50° C., ramp to 160° C.

Example 2: Racemic ethyl-4-(hydroxyimino)-2-methylbutanoate (Racemic Compound 2-b-Et) from ethyl (2R)-2-methyl-4-oxobutanoate (Racemic Compound 2-c-Et)

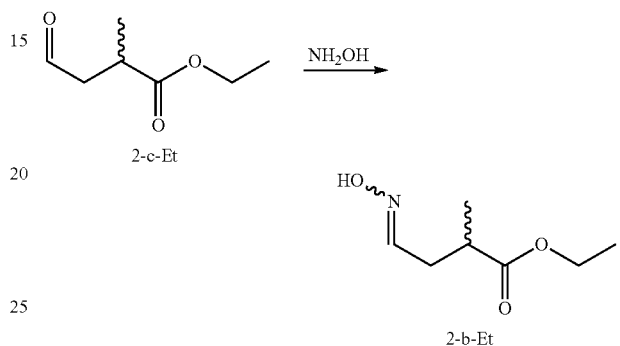

Compound (2-c-Et) (1.9 g, 13.17 mmol) was dissolved in acetonitrile (4 ml) then hydroxylamine 50% in water (14.50 mmol) was added and stirred over 40 minutes. Further hydroxylamine 50% in water (1.6 mmol) was added and the reaction was worked up after 20 minutes by extraction (2×10 mL DCM/water). The solvent was evaporated and 2.1 g of racemic compound (2-b-Et) was obtained as a liquid (100%).

$\delta_H$ (400 MHz, CDCl$_3$) 1.25 (6H), 2.34 (1H), 2.64 (2H), 4.15 (2H), 7.45, 6.78 (1H)

GC (FID), Rt=7.39 min; Column (30 m×0.32 mm×2.5 um); 50° C., ramp to 310° C.

Example 3: Racemic ethyl-2-methyl-4-nitrobutanoate (Racemic Compound 2-a-Et) from racemic ethyl-4-(hydroxyimino)-2-methylbutanoate (Racemic Compound 2-b-Et)

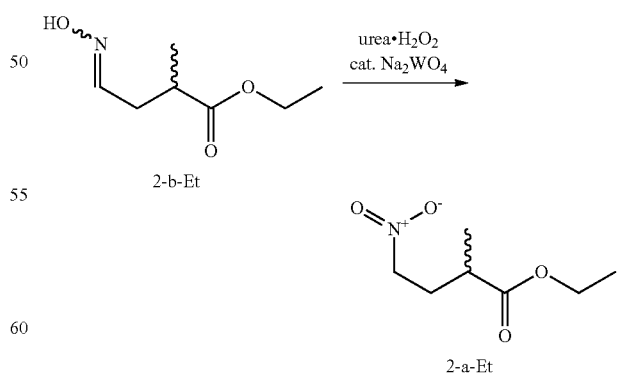

Compound (2-b-Et) (0.3 g, 1.88 mmol) was dissolved in methanol (4 ml) then sodium tungstate dihydrate (310 mg, 0.94 mmol) and urea hydrogen peroxide (532 mg, 5.65 mmol) were added and the stirred reaction mixture heated to 50° C. and stirred for 2 h. Compound (2-a-Et) was not isolated for reasons of thermal safety, but could be used in solution as such for the next step.

$\delta_H$ (400 MHz, CDCl$_3$) 1.25 (6H), 2.10-2.20 (1H), 2.30-2.35 (1H), 2.50-2.60 (1H), 4.15 (2H), 4.40-4.50 (2H)

GC (FID), Rt=10.46 min; Column DB-XLB (30 m×0.3 mm, 1 μL layer); 80° C. to 150° C. over 7 mins, hold for 2 mins, ramp to 240° C. over 2.25 mins.

Example 4: Racemic ethyl-2-methyl-4-nitrobutanoate (Racemic Compound 2-a-Et) from Ethyl Methacrylate

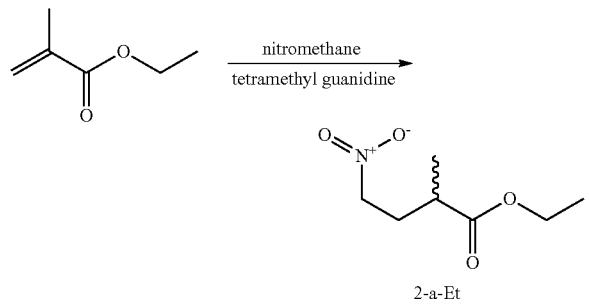

To a solution of ethyl methacrylate (45 g, 0.394 mol) in nitromethane (1203 g, 19.71 mol), tetramethyl guanidine (9.08 g, 0.079 mol) was added at room temperature. The reaction mixture was stirred at 25° C. for 24 hr. The reaction mass was then diluted with TBME (675 mL) and quenched with 1.5N HCl solution (135 mL), stirred for 0.5 h. Saturated brine solution (210 mL) was added and the mixture stirred for 20 min. The organic layer was separated and washed with brine solution (280 mL). The organic layer containing the mixture of MTBE and nitromethane was concentrated under vacuum at a temperature below 30° C. The crude was stripped off with toluene (90 mL). Crude product was then purified by high vacuum fractional distillation (maximum jacket temperature set to 100° C. for safety reasons) using a Vigreux column to give 42.6 g racemic 4 (61.6% yield).

$\delta_H$ (400 MHz, CDCl$_3$) 1.25 (6H), 2.10-2.20 (1H), 2.30-2.35 (1H), 2.50-2.60 (1H), 4.15 (2H), 4.40-4.50 (2H)

GC (FID), Rt=12.82 min, purity 95.98 A %; Column DB-624 (30 m×0.53 mm×3 um); 70° C. for 5 mins, 50-225° C. ramp at 15° C./min, hold for 10 mins, 225-250° C. ramp at 30° C./min, hold for 2 mins

GCMS: MH$^+$ 176.2

Example 5: Ethyl (2R)-2-methyl-4-nitrobutanoate (Compound 2-a-R-Et) from Racemic ethyl-2-methyl-4-nitrobutanoate (Racemic Compound 2-a-Et) by Chiral Crystallisation

A)

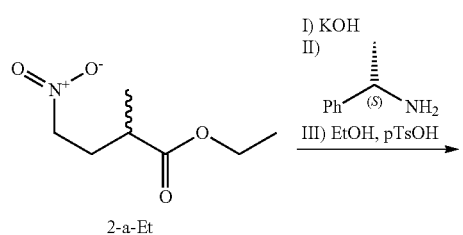

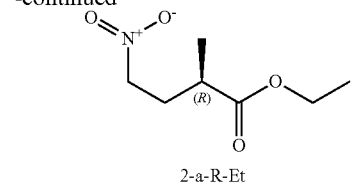

To an aqueous solution of KOH (48 g, 0.86 mol dissolved in 300 mL of water), racemic compound (2-a-Et) (100 g, 0.57 mol) was added at 25° C. in 30 min. The reaction mass was stirred at 25° C. for 24 h. The reaction mass was extracted with TBME (2×200 mL). The aqueous layer was cooled to 5-10° C. and acidified with 10% H$_2$SO$_4$ solution. Precipitated solid was filtered and washed with ethyl acetate (2×200 mL). The aqueous layer from the main filtrate was extracted with ethyl acetate (3×200 mL). The washings and extracts were combined and washed with water (2×200 mL) and brine solution (200 mL). The organic layer was dried over sodium sulphate and was concentrated under reduced pressure at 40° C. to give the crude carboxylic acid (69 g, 82% yield). Unreacted starting material could be recovered from the TBME layer and resubmitted for saponification.

A solution of the carboxylic acid (68 g, 0.462 mol) in TBME (340 mL) was slowly added to a solution of (S)-(−)-α-methylbenzylamine (27.2 g, 0.22 mol) in TBME (340 mL) at 25° C. within 20-30 min. During the addition, precipitation was observed. The reaction mixture was stirred at 25° C. for a further 3 h. The reaction mass was cooled to 0 to −5° C. and maintained for 2 h. After filtration, the precipitated salt was washed with chilled TBME (4×50 mL). Air drying for 1 h yielded the ammonium carboxylate diastereomerically enriched salt (26 g, 42% yield)

Optical rotation: [α]25=−3.0 [C=1, EtOH].

B)

To a solution of the ammonium carboxylate diastereomeric enriched salt (25 g, 0.093 mol) in ethanol (500 mL), p-toluene sulphonic acid monohydrate (17.7 g, 0.101 mol) was added at 25° C. The reaction mixture was stirred at 25° C. for 24 h and then heated to reflux at 80° C. for 3 h. The mixture was cooled to 40° C., the solvent completely evaporated and water was added (200 mL). It was further extracted with TBME (3×200 mL), and the combined organic layers were washed with NaHCO$_3$ solution (200 mL), water (200 mL) followed by brine solution (200 mL). The organic layer was dried over sodium sulphate and concentrated under reduced pressure at 40° C. to yield compound (2-a-R-Et) as a liquid (14 g, 85.8% yield).

GC (FID): 94.62 A %, Column HP-5 (30 m×0.32 mm), 0.251 um, 70° C. for 2 mins, ramp to 300° C. with 40° C./min, hold for 7 mins.

Optical rotation: [α]25=−5.254 [C=1, EtOH]

Chiral HPLC: Column: Chiralpak ID 5 um (250×4.6 mm). Mobile phase: n-Heptane/TBME/methanol 65:34:1. Flow rate: 1.000 ml/min. Detection UV: 220 nm Compound (2-a-Et) as (R)-enantiomer, Rt=9.2 min (88.5 A %); as (S)-enantiomer, Rt=7.6 min (11.5 A %)→77% ee $\delta_H$ (400 MHz, CDCl$_3$) 1.25 (6H), 2.10-2.20 (1H), 2.30-2.35 (1H), 2.50-2.60 (1H), 4.15 (2H), 4.40-4.50 (2H)

GCMS: MH$^+$176.2

Example 6: Ethyl (2R)-2-methyl-4-nitrobutanoate (compound 2-a-R-Et) from Racemic ethyl-2-methyl-4-nitrobutanoate (Racemic Compound 2-a-Et) by Chiral SMB Chromatography

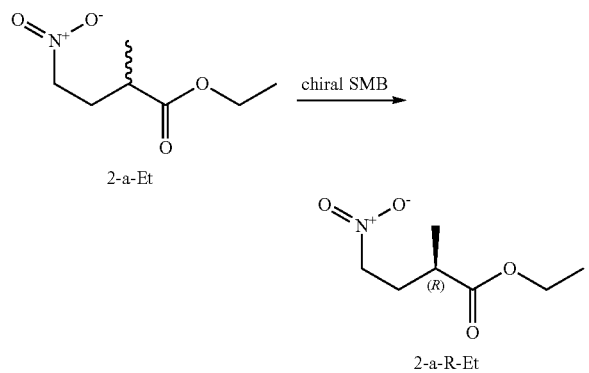

Feed preparation: 10 g/L in n-heptane/TBME/methanol 65:34:1

Preparative Chromatography:
Instrumentation: Bayer CC50 SMB Unit
Flow rates: Eluent 25.5 l/h; Feed 0.5 L/h; Extract 5.6 L/h; Raffinate 1.7 L/h; Recycle 18.7 L/h
Mobile phase: n-Heptane/TBME/methanol 65:34:1
Column: Chiralpak ID 20 um 8×(100×50 mm)
Switch time: 72 sec.
Analytical Chromatography:
Instrumentation: Shimadzu prominence HPLC system
Injection volume: 2/5/10 ul
Mobile phase: n-Heptane/TBME/methanol 65:34:1
Flow rate: 1.000 ml/min
Column: Chiralpak ID 5 urn (250×4.6 mm)
Detection UV: 220 nm
Results:
102 g racemate provided 49.7 g of recovered raffinate in two batches with purity of 99.0% ee and 98.1% ee as solutions in n-heptane. 10 m % TBME was added to the solutions to keep them homogeneous at 5° C. (28 m % and 41 m % solutions respectively).

Example 7a: Ethyl 5-ambo-(2R,4S)-5-([1,1'-biphenyl]-4-yl)-5-hydroxy-2-methyl-4-nitropentanoate (Compound 1-a-RS-Et) from Ethyl (2R)-2-methyl-4-nitrobutanoate (Compound 2-a-R-Et) and [1,1'-biphenyl]-4-carbaldehyde (Compound 3) using (R,R)-Woggon-ligand

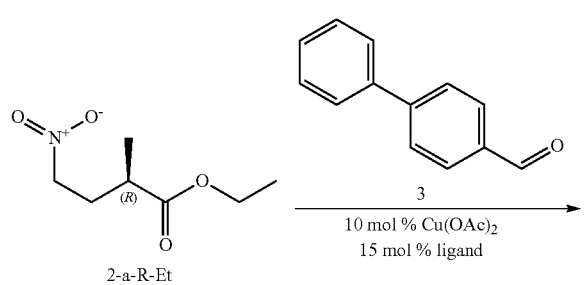

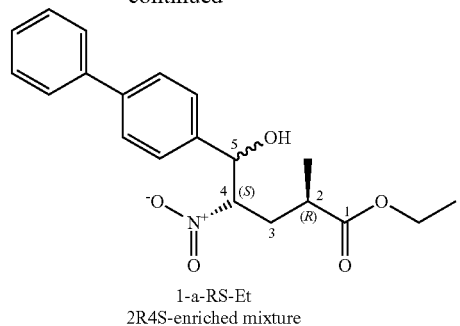

Copper(II)acetate (0.11 g, 0.63 mmol), (R,R)-Woggon-ligand (0.35 g, 0.95 mmol) and DBU (76 mg, 0.50 mmol) were added to THF (10 ml) under nitrogen and the dark green solution was stirred at room temperature for 20 mins. [1,1'-Biphenyl]-4-carbaldehyde, compound 3 (1.72 g, 9.42 mmol) was added and the solution was cooled to −45° C. After 10 mins of stirring compound (2-a-R-Et) (1.10 g, 6.28 mmol) was added over 1 min and the reaction was left to stir for 18 hrs. Further DBU (0.1 g, 0.66 mmol) was added. After a total reaction time of 30 hrs the reaction mixture was allowed to warm up to room temperature upon which citric acid solution was added (25 ml, 100 mg/ml). Ethyl acetate was added (5 ml) and the suspension extracted, providing an organic phase containing compound (1-a-RS-Et enriched mixture) (1.95 g, 86 m % (mass %) yield according to internal standard (1-methylnaphthaline)). The solution was evaporated to dryness and the residue could be used as such for the next step.

HPLC: RRR (30.65 min): 4.2 A %; RSS (31.25 min): 65.6 A %; RRS (31.79 min): 13.7 A %; RSR (32.28 min): 16.5 A %. Agilent Xbridge C18 column (3.5 μm, 3.0×150.0 mm). Mobile phases: A, $H_3PO_4$ in water (1.5 g/L); B, acetonitrile. Flow: 1 mL/min The four products were isolated by preparative chiral HPLC:

Compound (1-a-Et) as (2R,4S,5S)-isomer $\delta_H$ (400 MHz, $CDCl_3$) 1.15 (3H), 1.25 (3H), 1.78-1.86 (1H), 1.94-2.04 (1H), 2.33-2.41 (1H), 4.10-4.18 (2H), 4.95-5.02 (1H), 5.08 (1H, benzylic 5CH), 7.40 (1H), 7.45-7.51 (4H), 7.59-7.69 (4H)

Compound (1-a-Et) as (2R,4S,5R)-isomer $\delta_H$ (400 MHz, $CDCl_3$) 1.20 (6H), 2.15-2.36 (2H, +solvent), 2.43-2.50 (1H), 4.05-4.12 (2H), 4.88-4.93 (1H), 5.33 (1H, benzylic 5CH), 7.35-7.68 (9H)

Compound (1-a-Et) as (2R,4R,5S)-isomer $\delta_H$ (400 MHz, $CDCl_3$) 1.15 (3H), 1.25 (3H), 2.03-2.12 (1H), 2.39-2.50 (1H), 2.59-2.70 (1H), 4.05-4.16 (2H), 4.82 (1H), 5.30 (1H, benzylic 5CH), 7.40 (1H), 7.45-7.50 (4H), 7.58-7.66 (4H)

Compound (1-a-Et) as (2R,4R,5R)-isomer $\delta_H$ (400 MHz, $CDCl_3$) 1.04 (3H), 1.14 (3H), 1.42-1.51 (1H), 2.20-2.15 (2H), 3.96-4.04 (2H), 4.74-4.81 (1H), 5.01 (1H, benzylic 5CH), 7.29 (1H), 7.33-7.41 (4H), 7.48-7.58 (4H)

Example 7b: Ethyl 5-ambo-(2R,4S)-5-([1,1'-biphenyl]-4-yl)-5-hydroxy-2-methyl-4-nitropentanoate (Compound 1-a-RS-Et) from ethyl (2R)-2-methyl-4-nitrobutanoate (Compound 2-a-R-Et) and [1,1'-biphenyl]-4-carbaldehyde (Compound 3) using (R,R)-Sedel-ligand

Example 8: Ethyl 5-ambo-(2R,4S)-5-([1,1'-biphenyl]-4-yl)-4-{[(tert-butoxy)carbonyl]amino}-5-hydroxy-2-ethylpentanoate (Compound 1-b-RS-Et/Boc) from ethyl 5-ambo-(2R,4S)-5-([1,1'-biphenyl]-4-yl)-5-hydroxy-2-methyl-4-nitropentanoate (Compound 1-a-RS-Et)

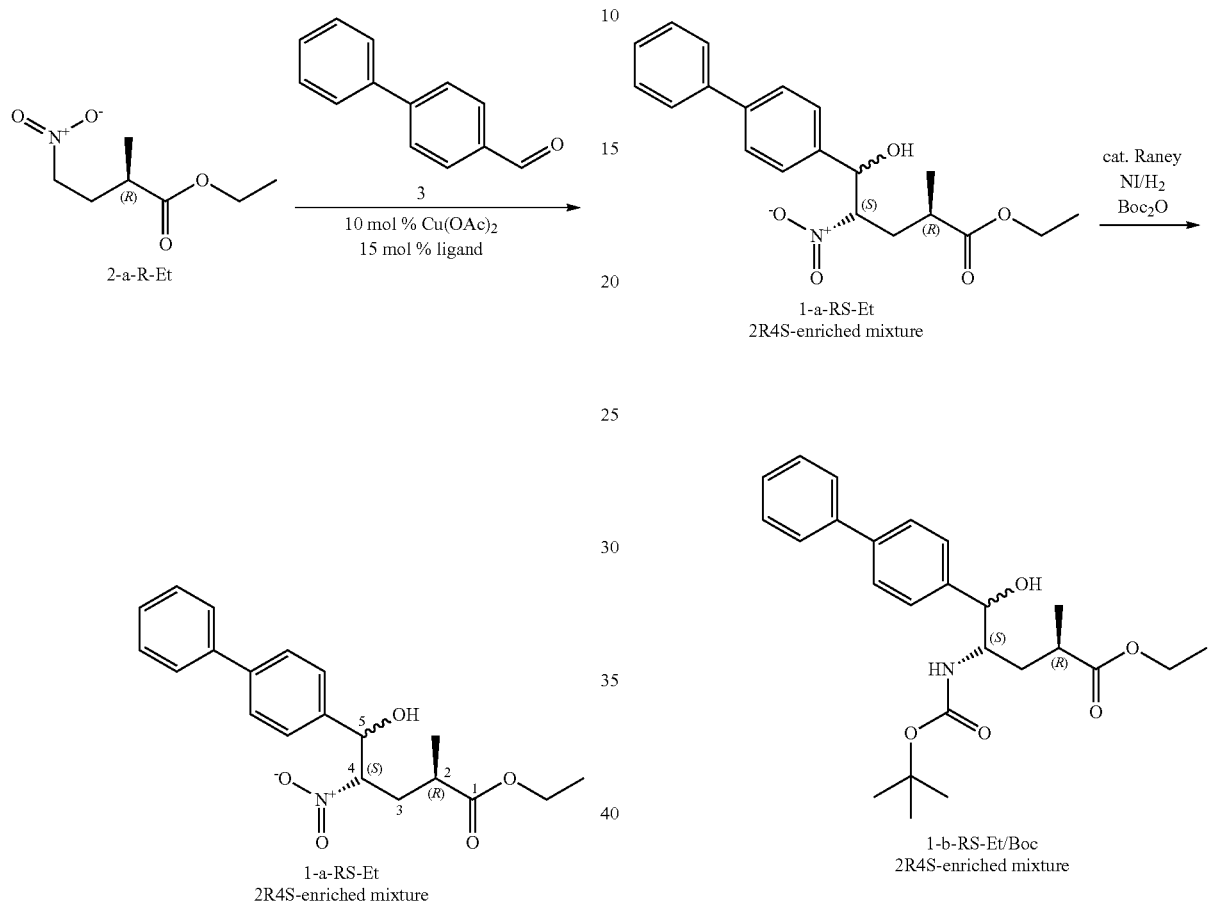

Copper(II)acetate (7.3 mg, 0.037 mmol), (R,R)-Sedel-ligand (20.4 mg, 0.044 mmol) and DBU (16.7 mg, 0.11 mmol) were added to THF (1.5 ml) under nitrogen and the dark green solution was stirred at room-temperature for 20 mins. The solution was cooled to −25° C. and [1,1'-biphenyl]-4-carbaldehyde, compound 3, (100 mg, 0.549 mmol) was added. After 2 mins of stirring compound 2-a-R-Et (64.1 mg, 0.366 mmol) was added and after 5 mins an IPC sample was taken for mini-quench to avoid retro-Henry reaction: the sample was added to a mixture of 10% aqueous citric acid and ethyl acetate and the upper organic phase taken for HPLC analysis, confirming full consumption of compound 2-a-R-Et and similar stereoselectivity to use of (R,R)-Woggon-ligand.

HPLC: RRR (30.65 min): 1.8 A %; RSS (31.25 min): 68.1 A %; RRS (31.79 min): 20.5 A %; RSR (32.28 min): 9.6 A %. Agilent Xbridge C18 column (3.5 μm, 3.0×150.0 mm). Mobile phases: A, $H_3PO_4$ in water (1.5 g/L); B, acetonitrile. Flow: 1 mL/min To a 2R4S-enriched mixture of compound 1-a-RS-Et (6.5 g, 18.19 mmol) and di-tert-butyldicarbonate (6.1 g, 27.95 mmol) in THF (60 ml) in a hydrogenation reactor was added Raney-nickel 3202 as 50% water slurry (4.0 g) under argon. The sealed reactor was then pressurized 5 times with nitrogen up to 4-5 bar before pressurization 5 times with hydrogen. The stirred slurry was heated to a jacket temperature of 43° C. and pressurized up to 4 bar with hydrogen over a 10 hr period. The reactor was depressurized, then flushed with nitrogen before filtration over cellulose microcrystalline powder. The filter cake was washed with THF (60 ml), avoiding suction to dryness. The filtrate was evaporated to dryness, and the residue could be used as such for the subsequent chemical step, or else purified by silica column chromatography (n-heptane/ethylacetate gradient from 9:1 to 4:1, UV-detection at 280 nm).

$δ_H$ (400 MHz, $(CD_3)_2SO$) 0.97-1.34 (15H), 1.69-1.80 (1H), 2.30-2.47 (1H), 3.50-3.76 (1H), 3.88-4.09 (2H), 4.42-4.63 (1H), 5.30-5.47 (1H), 6.16-6.61 (1H), 7.30-7.479 (5H), 7.55-7.67 (4H)

Example 9: (3R,5S)-5-([1,1'-Biphenyl]-4-ylmethyl)-3-methylpyrrolidin-2-one (Compound 7-RS—H) from ethyl 5-ambo-(2R,4S)-5-([1,1'-biphenyl]-4-yl)-4-{[(tert-butoxy)carbonyl]amino}-5-hydroxy-2-ethylpentanoate (Compound 1-b-RS-Et/Boc)

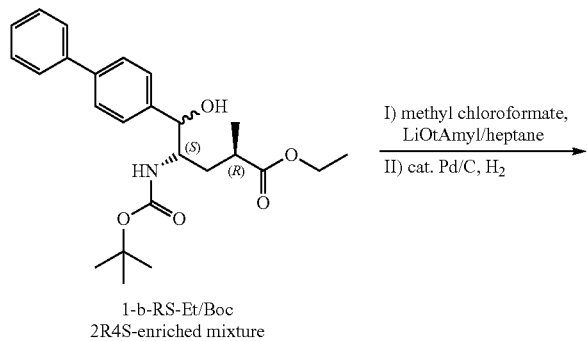

1-b-RS-Et/Boc
2R4S-enriched mixture

I) methyl chloroformate, LiOtAmyl/heptane
II) cat. Pd/C, H$_2$ acetate (0.92 ml) to which water was added (0.4 ml) followed by palladium 5% on charcoal (type 437, 50% water-wet, 60 mg, 14 µmol). The vessel was sealed and inertised with nitrogen, then repeatedly pressurized with hydrogen, fixing the pressure at 11 bar at 75° C., at which it was stirred for 20 hrs. The reactor was depressurized, then flushed with nitrogen before filtration over cellulose microcrystalline powder. The filter cake was washed with isopropyl acetate (2 ml). The filtrate was evaporated to dryness to provide white crystals of compound (7-H) as a mixture enriched in the desired (3R,5S)-isomer (150 mg, 66%).

HPLC: 61:39 A % compound (7-RS—H): (3R,5S)-diastereomer; column ReproShell C18, 75 mm×3 mm, pH3, ACN/MeOH-2:3, 0.8 ml/min, 254 nm.

LCMS: MH$^+$266.2

Example 10: (R,R)-Sedel Ligand

Overview for the synthesis of unsymmetrical DPEN-salen-ligands via N-alkylation approach

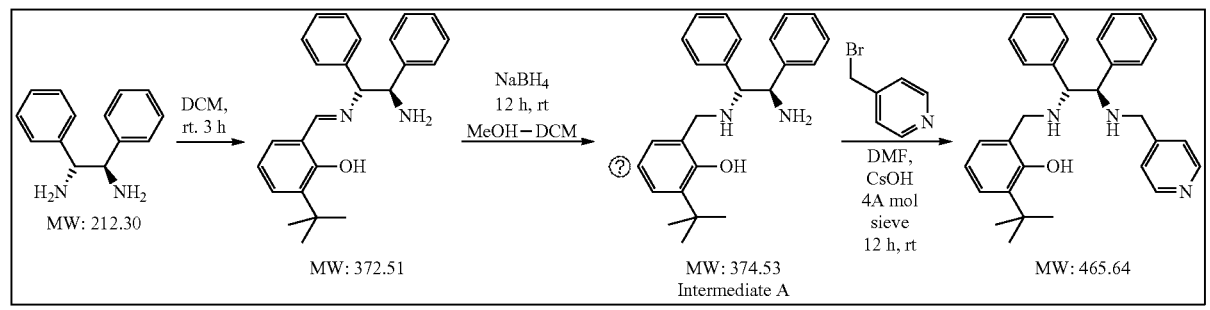

-continued

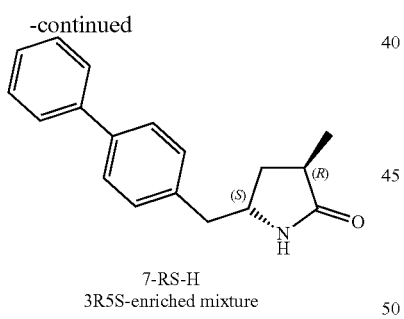

7-RS-H
3R5S-enriched mixture

Compound (1-b-RS-Et/Boc) crude residue (300 mg, 0.70 mmol) was dissolved in isopropyl acetate (1 ml) at room temperature and then cooled to 0-2° C. in an ice-bath. Methylchloroformate (70 mg, 0.74 mmol) was added dropwise over 5 mins, followed by addition of lithium tert-amylate (340 mg as a 40% solution in heptane, 1.45 mmol), upon which the mixture was stirred at 0-2° C. for 3 hrs. Water (0.6 ml) was premixed with ethanolamine (42 mg, 0.70 mmol) and dosed onto the reaction mixture, with stirring for 30 mins in order to quench the excess methylchloroformate. Isopropyl acetate (1 ml) was added and the organic phase separated, then dried over sodium sulfate and the solvent removed by evaporation to provide the crude acylated compound (1-b-RS-Et/Boc).

Crude acylated compound (1-b-RS-Et/Boc) (270 mg, 0.56 mmol) in a hydrogenation vessel was dissolved in isopropyl (1R,2R)-(+)-1,2-diphenyl-1,2-ethanediamine is commercially available.

3-tert-Butyl-2-hydroxybenzaldehyde is commercially available.

Synthesis of Mono-Schiff Base

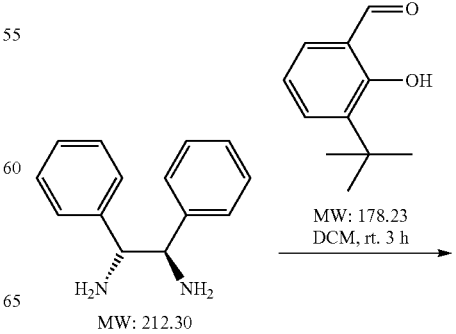

MW: 212.30

MW: 178.23
DCM, rt. 3 h

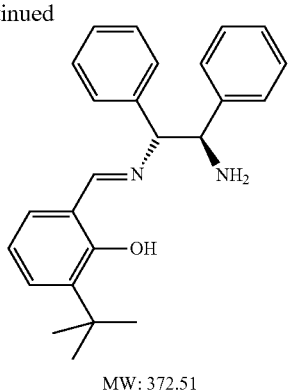

MW: 372.51

To a stirred solution of (1R,2R)-(+)-1,2-diphenyl-1,2-ethanediamine (9.4 mmol, 1.0 equiv.) in dry dichloromethane (100 ml), a solution of 3-tert-butyl-2-hydroxybenzaldehyde (9.4 mmol, 1.0 equiv.) in dry dichloromethane (100 ml) was added dropwise over a period of 40 min at room temperature. The resulting yellowish solution was allowed to stir at room temperature for additional 3 h. Conversion was determined by $^1$H-NMR. No purification was performed on this stage of the synthesis. The imine appeared as a mixture of 7:1—E/Z.

$^1$H-NMR: (major; 400 MHz, CDCl$_3$): 1.48 (s, 9H), 4.33 (d, J=7.6 Hz, 1H), 4.44 (d, J=7.6 Hz, 1H), 6.81 (t, J=7.6 Hz, 1H), 7.10 (dd, J=7.6, 1.4 Hz, 1H), 7.14-7.23 (m, 10H), 7.35 (dd, J=7.7, 1.3 Hz, 1H), 8.43 (s, 1H), 13.83 (s, OH).

Reduction of Imine to Mono-Salen Intermediate A

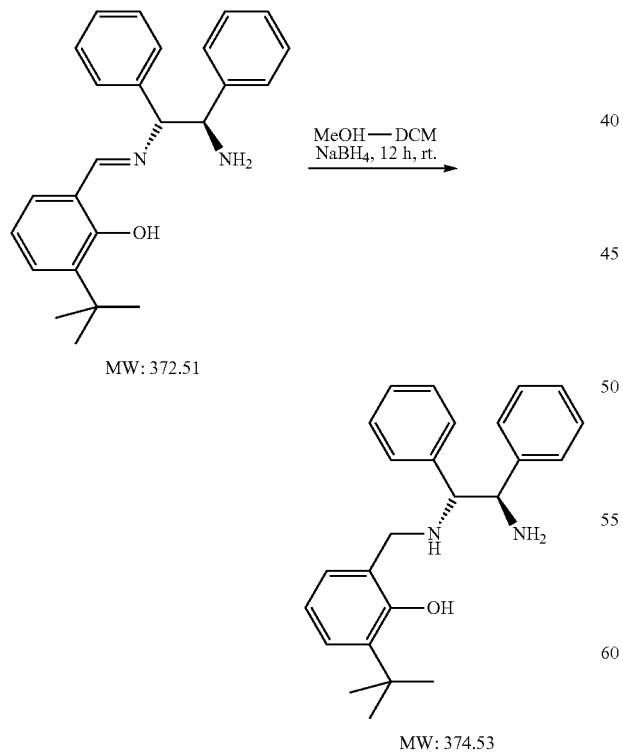

The solution of the imine intermediate (9.4 mmol, 1.0 equiv.) was concentrated to 50% of the volume and diluted with dry methanol (30 ml). Then solid NaBH$_4$ (47.0 mmol, 5.0 equiv.) was added in small portions at room temperature and the mixture was allowed to stir at room temperature for 12 h. The yellowish solution turns colourless overtime. Conversion was determined by TLC (SiO$_2$; n-hexane:ethyl acetate=1:1) and $^1$H-NMR.

The solvent was removed under vacuum and the residue was extracted with aqueous saturated K$_2$CO$_3$ solution and DCM to remove residual borane. The water phase was saturated with NaCl and extracted with DCM (5×50 ml). The combined organic layers were dried over Na$_2$SO$_4$ and concentrated under reduced pressure to give yellow oil. The oil was dissolved in Et$_2$O (100 ml) and treated with HCl (1M in Et$_2$O, 20 ml, 2.1 equiv.) and stirred for 30 min at room temperature. The ammonium salts precipitates and are filtered off and washed with Et$_2$O (2×20 ml). The ammonium salt was finally neutralized by extraction with DCM and saturated aqueous K$_2$CO$_3$ solution. The organic layer was dried over Na$_2$SO$_4$ and concentrated under reduced pressure to give mono-salen intermediate A as a colourless foam in 88% yield.

$^1$H-NMR: (400 MHz, CDCl$_3$): 1.40 (s, 9H), 3.59 (d, J=13.3 Hz, 1H), 3.79-3.84 (m, 2H), 4.16 (d, J=6.6 Hz, 1H), 6.63-6.71 (m, 2H), 7.15 (m, 5H), 7.24 (m, 6H).

N-Alkylation of Intermediate A

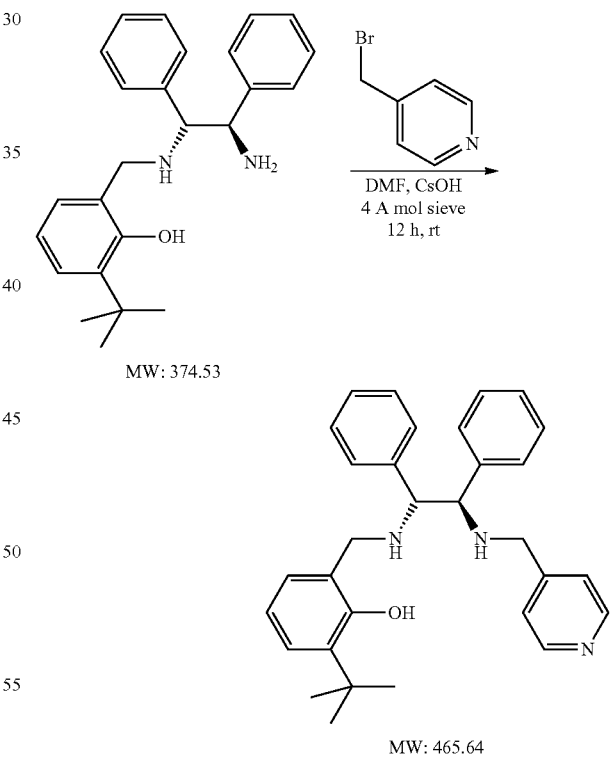

To a suspension of intermediate A (970 mg, 2.59 mmol, 1 equiv.) and activated powdered 4 Å molecular sieves (1.0 g) in anhydrous DMF (8 ml) was added dried cesium hydroxide monohydrate (1.09 g, 6.47 mmol, 2.5 equiv.) and the mixture was vigorously stirred for 30 min. 4-(Bromomethyl)-pyridine hydrobromide (721 mg, 2.85 mmol, 1.1 equiv.) was added to the brown suspension, and the reaction was allowed to stir at room temperature for 12 h. The reaction mixture was filtered to remove undissolved solids and washed with ethyl acetate (2×20 mL). The filtrate was concentrated, and the residue was extracted with 1N NaOH and ethyl acetate (4×20 mL).

The combined organic layers were dried over Na$_2$SO$_4$, filtered, and evaporated. The resulting crude mixture was purified by column chromatography (SiO$_2$; n-hexane:ethyl acetate –(1:1)+5 vol % NEt$_3$) to afford the product (796 mg, 1.71 mmol, 66%) as a yellow oil.

$^1$H-NMR: (400 MHz, CDCl$_3$): 1.49 (s, 9H), 3.53 (d, J=12.9 Hz, 1H), 3.64 (d, J=13.3 Hz, 1H), 3.72 (d, J=14.7 Hz, 1H), 3.84 (m, 3H), 6.70-6.75 (m, 2H), 7.03-7.09 (m, 4H), 7.17-7.24 (m, 9H), 8.52 (d, J=4.8 Hz, 2H).

$^{13}$C-NMR: (400 MHz, CDCl$_3$): 29.6, 34.8, 50.0, 50.9, 67.5, 68.4, 118.4, 123.0, 123.3, 126.1, 126.7, 127.6, 127.7, 127.8, 127.9, 128.4, 128.5, 137.0, 138.9, 139.8, 149.1, 149.9, 156.9.

The invention claimed is:

1. A compound of formula (1), or a salt thereof,

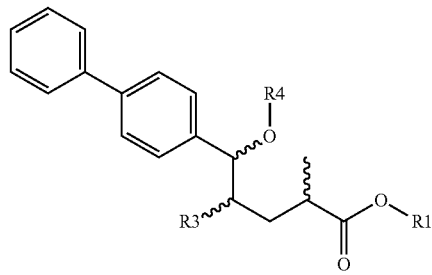
(1)

wherein:

R1 is hydrogen or C$_1$-C$_6$-alkyl;

R3 is —NO$_2$ or —NR'R'', wherein R' and R'' are independently of each other hydrogen or a nitrogen protecting group; and R4 is selected from hydrogen, C$_1$-C$_6$-carbonyl, C$_1$-C$_6$-alkoxycarbonyl, and a sulphonyl group.

2. The compound according to claim 1, or a salt thereof, wherein the compound has a configuration according to formula (1-R):

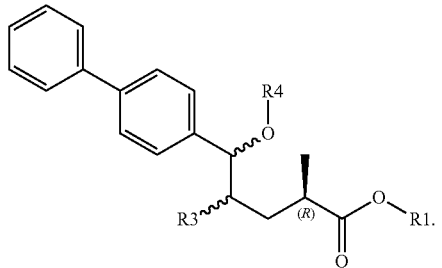
(1-R)

3. A process for producing a compound of claim 1 having a formula (1-a),

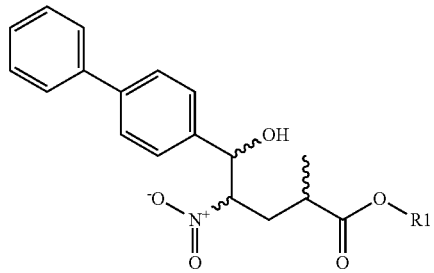
(1-a)

comprising reacting a compound of formula (2-a)

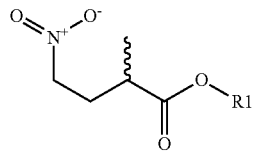
(2-a)

wherein R1 is hydrogen or C$_1$-C$_6$-alkyl, with a compound of formula (3)

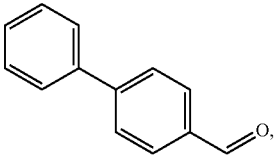
(3)

wherein the reaction of compound of formula (2-a) with the compound of formula (3) is performed in the presence of a metal complex catalyst comprising a metal and a chiral ligand.

4. The process according to claim 3, wherein the metal is Cu and the chiral ligand is selected from the group consisting of camphor-pyridine ligands, DAC ligands, and DPEN ligands.

5. The process according to claim 3, wherein the compound of formula (2-a),

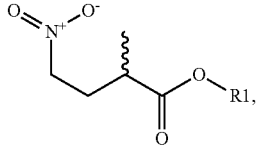
(2-a)

is prepared by oxidation of a compound of formula (2-b)

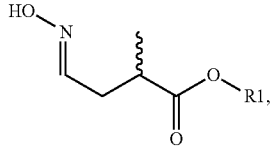
(2-b)

said oxidation comprising the use of an oxidant and optionally a catalyst, and wherein in the above formulae R1 is hydrogen or $C_1$-$C_6$-alkyl.

6. The process according to claim 5, wherein the compound of formula (2-b),

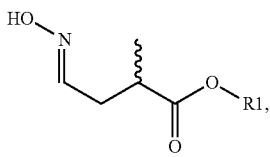

(2-b)

is prepared by oxime formation of a compound of formula (2-c),

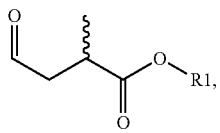

(2-c)

said oxime formation comprising the use of hydroxylamine or a salt thereof, and wherein in the above formulae R1 is hydrogen or $C_1$-$C_6$-alkyl.

7. The process according to claim 6, wherein the compound of formula (2-c),

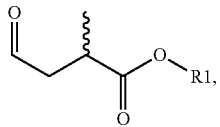

(2-c)

is prepared by hydroformylation, of a methacrylate of formula (2-d)

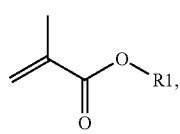

(2-d)

said hydroformylation comprising the use of carbon monoxide, hydrogen and optionally a metal complex catalyst, and wherein in the above formulae R1 is hydrogen or $C_1$-$C_6$-alkyl.

8. The process according to claim 3, wherein the compound of formula (2-a),

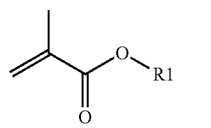

(2-a)

is prepared by treating a compound of formula (2-d)

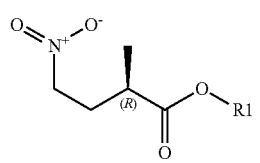

(2-d)

with nitromethane, optionally followed by a chiral separation of the compound of formula (2-a) to obtain the compound of formula (2-a-R),

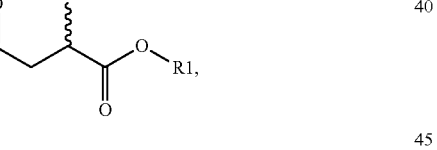

(2-a-R)

wherein the chiral separation is carried out by chiral simulated moving bed (SMB) chromatography, and wherein in the above formulae R1 is hydrogen or $C_1$-$C_6$-alkyl.

9. A process for producing a compound of claim 1 having a formula (1-b),

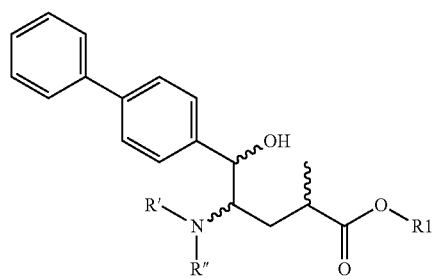

(1-b)

comprising hydrogenation of a compound of formula (1-a)

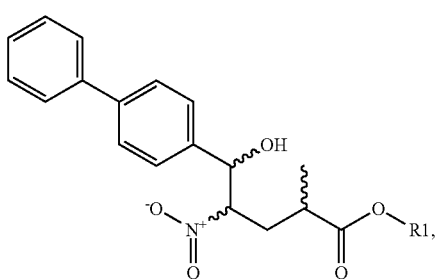

(1-a)

optionally in the presence of a nitrogen protecting agent.

10. The process according to claim 9, wherein the compound of formula (1-a) is produced by the process according to claim 3.

11. A process for producing a compound of formula (6)

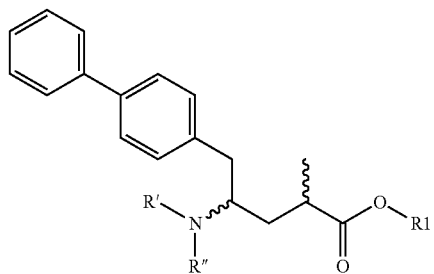

(6)

wherein R' and R" are independently of each other hydrogen or a nitrogen protecting group, and R1 is hydrogen or $C_1$-$C_6$-alkyl, said process comprising taking a compound of formula (1-b)

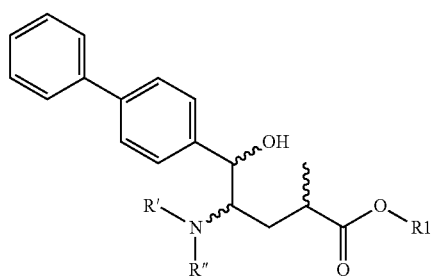

(1-b)

wherein R' and R" are independently of each other hydrogen or a nitrogen protecting group, and R1 is hydrogen or $C_1$-$C_6$-alkyl, optionally treating the compound of formula (1-b) with an OH-activating agent to obtain a compound of formula (1-d)

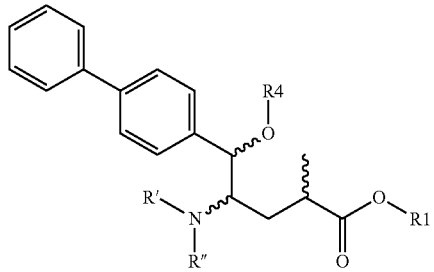

(1-d)

wherein R' and R" are independently of each other hydrogen or a nitrogen protecting group,
R1 is hydrogen or $C_1$-$C_6$-alkyl, and
R4 is an OH-activating group, and
subjecting the compound of formula (1-b) or (1-d) to a hydrogenation reaction to obtain the compound of formula (6).

12. The process according to claim 11, wherein the compound of formula (1-b) or the compound of formula (1-d) wherein R4 is hydrogen, is produced by the process according to claim 9.

13. The process according to claim 11, wherein the hydrogenation reaction to obtain a compound of formula (6) is carried out via the intermediate compound of formula (7)

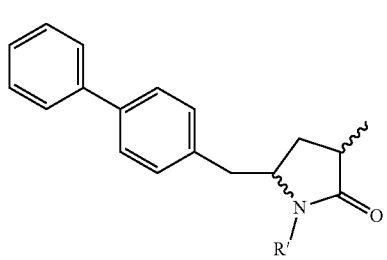

(7)

wherein R' is hydrogen or a nitrogen protecting group, which is reacted with a ring opening agent, wherein the ring opening agent comprises water or a $C_1$-$C_6$-alkanol, to obtain a compound of formula (6); and
wherein the obtained compound of formula (6) is optionally further reacted to obtain a compound of formula (8),

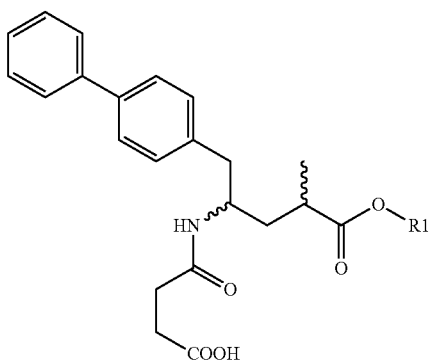

(8)

wherein R1 is hydrogen or $C_1$-$C_6$-alkyl.

14. The process according to claim 4, wherein the chiral ligand is a compound of formula (4a), or a compound of formula (4b),
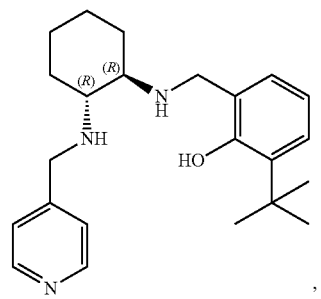
(4a)
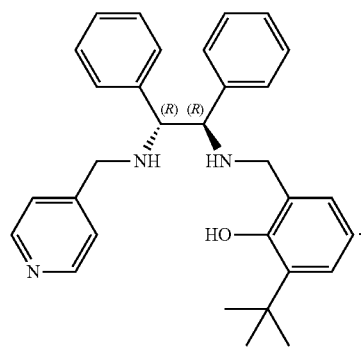
(4b)
\* \* \* \* \*